(12) United States Patent
Striemer et al.

(10) Patent No.: US 12,102,872 B1
(45) Date of Patent: Oct. 1, 2024

(54) APPARATUS AND METHOD FOR MONITORING AND IMPROVING ATHLETIC PERFORMANCE

(71) Applicant: Bryan L. Striemer, Zumbrota, MN (US)

(72) Inventors: Bryan L. Striemer, Zumbrota, MN (US); Charles A. Lemaire, Apple Valley, MN (US)

(73) Assignee: Bryan L. Striemer, Zumbrota, MN (US)

( * ) Notice: Subject to any disclaimer, the term of this patent is extended or adjusted under 35 U.S.C. 154(b) by 0 days.

(21) Appl. No.: 18/106,873

(22) Filed: Feb. 7, 2023

Related U.S. Application Data

(60) Provisional application No. 63/308,961, filed on Feb. 10, 2022.

(51) Int. Cl.
*A63B 24/00* (2006.01)

(52) U.S. Cl.
CPC .. *A63B 24/0006* (2013.01); *A63B 2024/0012* (2013.01); *A63B 2220/12* (2013.01);
(Continued)

(58) Field of Classification Search
CPC ........ A63B 24/0006; A63B 2024/0012; A63B 2220/12; A63B 2220/18; A63B 2220/44; A63B 2220/76; A63B 2220/836
(Continued)

(56) References Cited

U.S. PATENT DOCUMENTS

| | | | |
|---|---|---|---|
| 6,148,262 | A | 11/2000 | Fry |
| 8,011,242 | B2 | 9/2011 | O'Neill et al. |

(Continued)

FOREIGN PATENT DOCUMENTS

| | | | | |
|---|---|---|---|---|
| WO | WO-2012148056 A1 | * | 11/2012 | ......... B60C 23/0416 |

OTHER PUBLICATIONS

Braeckevelt, et al., "The Need for Data-Driven Bike Fitting: Data Study of Subjective Expert Fitting", "download at: www.researchgate.net/publication/335976683_The_Need_for_Data-Driven_Bike_Fitting_Data_Study_of_Subjective_Expert_Fitting", Sep. 2019, Publisher: icSports 2019, the 7th International Conference on Sport Sciences Research and Technology.

(Continued)

*Primary Examiner* — Quan Zhen Wang
*Assistant Examiner* — Mancil Littlejohn, Jr.
(74) *Attorney, Agent, or Firm* — Charles A. Lemaire; Lemaire Patent Law Firm, P.L.L.C.

(57) ABSTRACT

Apparatus and method for measuring angles, such as foot angle at each of a plurality of positions during a plurality of successive strides during activity such as bicycling or running. Optionally, acceleration and gyroscopic/rotational data is wireless received from a foot-mounted sensor module having accelerometers for acceleration measurements in orthogonal directions and gyroscope sensors to provide rotational measurements around orthogonal axial directions; and a processor that calculates foot angles at a plurality of successive positions within each of a plurality of strides of a human user during an athletic activity; and an output device in the personal electronic device that presents human-perceptible indications based on the calculated foot-angle data. In some embodiments, the output data is presented visually and/or audibly. In some embodiments, stereo audio indications provide different audio indications to the user's left and right ears that correspond to different foot-angle data from the user's left and right feet.

21 Claims, 18 Drawing Sheets

(52) U.S. Cl.
CPC ....... *A63B 2220/18* (2013.01); *A63B 2220/44* (2013.01); *A63B 2220/76* (2013.01); *A63B 2220/836* (2013.01)

(58) Field of Classification Search
USPC ........................................................ 340/432
See application file for complete search history.

(56) References Cited

U.S. PATENT DOCUMENTS

| | | |
|---|---|---|
| 8,036,826 B2 | 10/2011 | Macintosh et al. |
| 8,122,773 B2 | 2/2012 | Wyatt et al. |
| 8,899,110 B2 | 12/2014 | Matsumoto |
| 10,835,778 B2 | 11/2020 | Kaji et al. |
| 2008/0200310 A1* | 8/2008 | Tagliabue ............ A61B 5/7405 342/357.57 |
| 2017/0003311 A1* | 1/2017 | Lay ......................... B62J 50/22 |
| 2017/0050080 A1* | 2/2017 | Mizuochi ............... G16H 20/30 |
| 2020/0114242 A1* | 4/2020 | Carlson ............. A63B 71/0686 |
| 2023/0271059 A1* | 8/2023 | Chen .................... A61B 5/1114 482/8 |

OTHER PUBLICATIONS

Maruyama, et al., "Riding Motion Capture System Using Inertial Measurement Units with Contact Constraints", "International Journal of Automation Technology", Jul. 5, 2019, pp. 506-516, vol. 13, No. 4, Publisher: https://doi.org/10.20965/ijat.2019.p0506.

\* cited by examiner

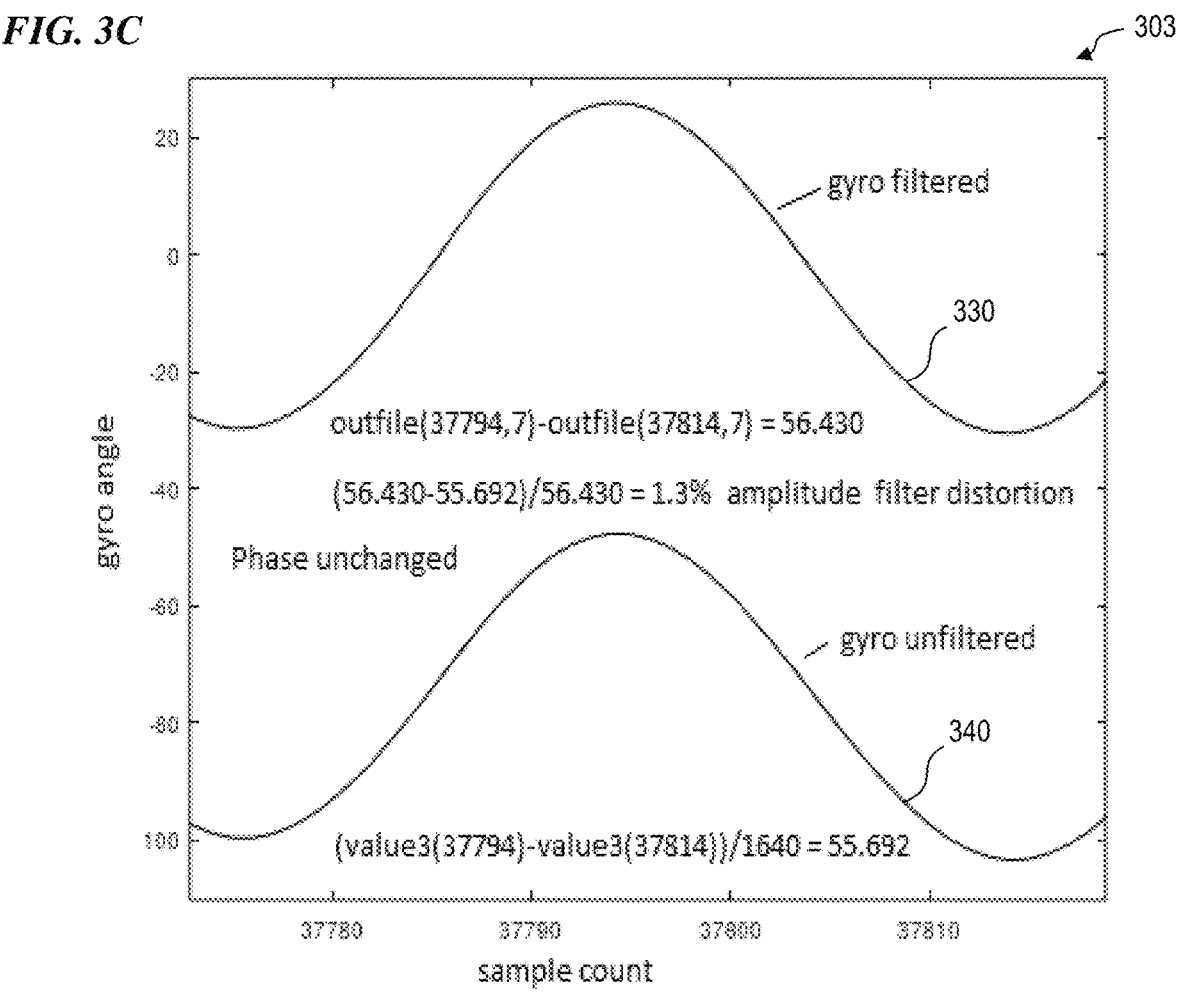

*A QUICK LOOK AT THE SAMPLE RATE OF ONE EMBODIMENT, AND TYPICAL AZ/GX WAVEFORMS. THIS CHART IS AT ABOUT 70 PEDAL STRIDES PER MINUTE AND THE WORST CASE ERROR WILL BE ABOUT 1 DEGREE OFF.*
*AT 90 PEDAL STRIDES PER MINUTE, IT WOULD BE JUST LESS THAN 2 DEGREES ERROR.*
*THIS INDICATES THAT EVEN AS FEW AS 50 SAMPLES PER SECOND IS NOT ONE OF THE BIG AREAS OF CONCERN.*

Leg-thigh (knee) angle

Torso angle (forward angle relative to horizontal, as shown).

In contrast, pelvic and torso rocking / rotation is left-right, perpendicular to the plane of the torso angle (see histograms in FIG. 20C and FIG 20D).

APPARATUS AND METHOD FOR MONITORING AND IMPROVING ATHLETIC PERFORMANCE

CROSS-REFERENCE TO RELATED APPLICATION

This application claims priority benefit, under 35 U.S.C. § 119(e), of U.S. Provisional Patent Application No. 63/308,961, filed Feb. 10, 2022 by Bryan L. Striemer et al. and titled "Apparatus and method for monitoring and improving athletic performance," which is incorporated herein by reference in its entirety.

FIELD OF THE INVENTION

The present invention relates to monitoring and improving athletic performance and more particularly to an apparatus and a method for receiving data that includes two or more parameters relating to orientation, acceleration, compass direction, and the like, processing the data to obtain angles of one or more body parts of the athlete, and providing human perceptible indicia to the athlete during and/or after an athletic performance.

BACKGROUND OF THE INVENTION

U.S. Pat. No. 6,148,262 issued to Fry on Nov. 14, 2000 with the title "Sports computer with GPS receiver and performance tracking capabilities" and is incorporated herein by reference. U.S. Pat. No. 6,148,262 describes a "sports computer having an integral global satellite positioning (GPS) receiver and computer interfacing capability enables functional and/or performance characteristics to be tracked and analyzed as a function of geographical position and/or elevation. The computer includes mounting means and/or interfaces to one or more sensors to measure operational and/or physiological parameters such as heart rate, or weather conditions such as temperature. Means are provided for downloading the stored geographical and sensor parameters to an external personal computer so that the data collected during a workout may be reviewed and analyzed on the screen of the PC. Preferably, map data may also be stored enabling the collected data to be viewed relative to the map information, for example, in superposition."

U.S. Pat. No. 8,011,242 issued to O'Neill et al. on Sep. 6, 2011 with the title "System and device for measuring and analyzing forces applied by a cyclist on a pedal of a bicycle" and is incorporated herein by reference. U.S. Pat. No. 8,011,242 describes "a sensor device for determining forces exerted by a cyclist on a pedal of a bicycle is provided. The sensor device includes a plurality of sensors coupled to a substrate, and wiring coupled to the sensors and the substrate, wherein the sensors, the substrate, and the wiring are housed inside a pedal spindle coupled to the pedal. The sensor device may also be used in a system for improving a pedaling technique of a cyclist."

U.S. Pat. No. 8,036,826 issued to MacIntosh et al. on Oct. 11, 2011 with the title "Sports sensor" and is incorporated herein by reference. U.S. Pat. No. 8,036,826 describes a "data logger for a monitoring sports, which includes an accelerometer, a gyro sensor to sense angular displacement, a GPS unit to sense position and velocity, a magnetometer to sense direction of movement, a heart rate monitor, and a controller programmed to manipulate the data and provide a display of the heart rate, speed, and other sport parameters. The data can be stored or transmitted to a remote computer for use by the coach. The device is useful in football codes, athletics, swimming, snow sports and cycling."

U.S. Pat. No. 8,122,773 issued to Wyatt et al. on Feb. 28, 2012 with the title "Systems and methods of power output measurement" and is incorporated herein by reference. U.S. Pat. No. 8,122,773 describes "systems and methods for measuring power output, as in an athletic activity such as cycling. One embodiment relates to a force sensing device configured to be mounted on the bottom surface of a shoe as part of a mechanical linkage through which force is exerted. For cycling, the force sensor is mounted on the bottom surface of a cycling shoe and fitted with a cleat that interlockingly engages a bicycle pedal. To measure both positive and negative pressures on the pedal, the force sensor is pre-stressed with a compressive load to an intermediate point in its dynamic range. Strains that further compress or decompress the force sensor can thus be measured. The computing module mathematically converts the measured pressures, positive and negative, to a measurement of total power exerted by the rider. In addition, the computing module may utilize cyclical regularities in the signal to compute the rider's cadence (pedal revolutions per unit of time). Data from the force sensor is transmitted wirelessly to a remote display where it can be viewed by the rider."

U.S. Pat. No. 10,835,778 issued to Kaji et al. published on Nov. 17, 2020 with the title "Motion capture system, motion capture program and motion capture method" and is incorporated herein by reference. U.S. Pat. No. 10,835,778 describes a display and output performed in such a manner as to allow complex body motions to be comprehended instantaneously. There are provided: a plurality of body motion sensors which are worn on a wearer's parts subject to cyclic motions and which are capable of measuring three-dimensional displacements and accelerations at the respective parts; a memory which records detection results as body motion data; a cycle extraction unit which extracts a cyclic motion of each of the body motion sensors on the basis of accumulated body motion data; an analysis unit which analyzes the characteristic of a change in angular velocity in the extracted cyclic motion; and displays that display or output the characteristic analyzed by the analysis unit in association with the rotation angle of the cyclic motion extracted by the cycle extraction unit.

United States Patent Application Publication 2017/0003311 by Lay et al. published Jan. 5, 2017 with the title "Method for detecting bicycle pedaling frequencies" and is incorporated herein by reference. Publication 2017/0003311 describes a method for detecting bicycle pedaling frequencies, in which an accelerometer of the body is used to detect the acceleration value of the pedal during pedaling, and the processing unit determines the periodical variations on acceleration increases and decreases, records the acceleration waveform, calculates the number of cycling in the pedal per minute based on the times that the sampled values within a unit time cross over the central line of the acceleration value, and also transfers tempo data to an electronic device by way of a wireless communication circuit and displays the pedaling frequency of the pedal via a screen so as to allow a user to promptly appreciate relevant information during riding and facilitate appropriate adjustments and controls on pedaling tempo and force.

U.S. Pat. No. 8,899,110 issued to Matsumoto on Dec. 2, 2014 with the title "Pedaling motion measuring device and pedaling motion sensor device" and is incorporated herein by reference. U.S. Pat. No. 8,899,110 describes a pedaling motion measuring device includes: a measurement body unit having a first sensor unit for sensing the number of rotation of a wheel by sensing the motion of the wheel of a bicycle, and second sensor units arranged at right and left crank arms for sensing magnitude and direction of a force applied to each of the right and left crank arms. The first work calculation unit calculates work performed by the bicycle based on the number of rotation of the wheel sensed by the first sensor unit. The second work calculation unit calculates work provided to the crank member by the user within a prescribed time, based on the magnitude and direction of the force applied to each of the right and left crank arms and sensed by the second sensor units. The efficiency calculation unit calculates the efficiency of the bicycle.

A conference paper "The Need for Data-Driven Bike Fitting: Data Study of Subjective Expert Fitting" by Jarich Braeckevelt et al. published September 2019 (available at www.researchgate.net/publication/335976683_The_Need_for_Data-Driven_Bike_Fitting_Data_Study_of_Subjective_Expert_Fitting) (hereinafter referred to as Braeckevelt et al.) is incorporated by reference. The Braeckevelt et al. paper describes attempts at adjusting bike parameters such as distances of handlebar drop, handlebar reach, seat height, and saddle setback. Their abstract states "In this research three cyclists were bike fitted by nine different bike fitting studios. It was hypothesised that, as different bike fitters use varying techniques and have different experience levels, the cyclist would be advised a different optimal position by these different bike fitters. The preconceived hypothesis was confirmed as the range of advised positions in both saddle height and setback was up to 3 cm. Data-driven bike fitting can help bring down these considerable differences amongst fitters and will be discussed in the last chapter."

A paper by Tsubasa Maruyama et al. titled "Riding Motion Capture System Using Inertial Measurement Units with Contact Constraints" can be found at website doi.org/10.20965/ijat.2019.p0506 (hereinafter referred to as Maruyama et al.) is incorporated by reference. The Maruyama et al. paper describes an optical motion-capture (MoCap) system supplemented with inertial-measurement unit (IMU)-based MoCap system that does not require any optical devices. The Maruyama et al. paper also describes the use of the optical MoCap and IMU MoCap measurements in a digital human (DH) robotic system that mimics human body motion, and the demonstration with a bicycle ergometer including the handles, seat, backrest, and foot pedals, as in general mobility products. The experiment revealed both the effectiveness and limitations of their proposed system.

There remains an unmet need for an improved method and apparatus, usable as a kit and/or downloadable software that is usable as-is or customizable to a small or large extent by the user, having a plurality of sensors that provide input data, analysis software that provides calculations of various parameters and comparisons to predetermined parameters (such as values determined to indicate ideal form, efficient use of muscles, and the like), and that output feedback to the human user and optionally one or more other persons in order to facilitate one-on-one and/or group competition, game play, self-improvement, training, etc.

SUMMARY OF THE INVENTION

In some embodiments, the present invention is configured for bicycling and provides real-time graphical, numerical, color-coded, and/or audible indications, which are continuous or repeating (e.g., via outputs from a personal electronic device such as a cell phone), of an athlete's foot-angles at different stride positions, or of foot angles as compared to some "ideal" foot angles, at a plurality of "o'clock positions" (e.g., in some embodiments, 12-o'clock, 3-o'clock, 6-o'clock, and 9-o'clock positions of each pedal revolution of a bicycle). The system compares actual foot angles to "ideal" foot angles, and provides gentle reinforcing or non-reinforcing stimulation to a human user (colloquially called "feedback" or "reward/punishment") to enable modification of behavior to achieve a more efficient and effective performance. In some embodiments, the present invention customizes gentle outputs and/or adaptively adjusts any stimulation outputs that do not result in reinforced positive changes in the user's form, minimizing the aversiveness of visual and/or audio stimulation that is output to help correct the user's form. In some embodiments, the software of the invention detects whether the stimulation presented to the user is resulting in improved form or efficiency, and if that stimulation is not resulting in better form, adaptively adjusts to use slightly or entirely different stimulation to better modify and improve the user's performance. With sufficient such guided practice (reinforcement of "ideal" foot angles and non-reinforcement of "other-than-ideal" foot angles), the natural reinforcing consequences of maintaining "ideal" foot angles—namely, improved speed—will come to "naturally" maintain such foot angles, with the present invention then perhaps serving a monitoring function, being utilized periodically to check, and correct if necessary, an athlete's foot angles.

In some such embodiments, the results are wirelessly uploaded to a "cloud-based" server for the purposes of an interactive competition or game between two or more competitors. In other embodiments, data from a plurality of sensors in one or more sensor modules are saved in the sensor module without the need to carry a cell phone during a workout of bicycling or running, and then later uploaded into a cell phone or personal computer, analyzed, and results of the analysis are presented to the human user and optionally uploaded across the internet for the purposes of an interactive competition or game between two or more competitors.

In some embodiments, the invention is configured to measure other parameters of bicycle riding, such as the forward-back (leaning) angle of a rider's back or the left-right (rocking) range of angles of the rider's pelvis over the bicycle saddle, and configured to provide real-time or periodic reinforcing-nature stimulation contingent upon approaches to "ideal" back angle or range of pelvis-rocking angles under various riding conditions (e.g., bicycling uphill, on a level path, downhill, or into curves of various angles, and/or under various wind conditions). In other embodiments, the invention is configured to measure important parameters of an athlete's physical performance in other athletic endeavors, such as swinging a tennis racket under various circumstances, swinging a baseball bat under various circumstances, and the like, and delivering reinforcing-nature stimulation contingent upon approaching "ideal" values of important physical parameters of the particular athletic endeavor, with such "ideal" values' being empirically selected, in some embodiments, on the basis of known best performance of athletes in the particular endeavor.

In some embodiments, the present invention includes (1) a housing (such as 130 of FIG. 1) that holds one or more motion, position, and/or orientation sensors (such as accelerometers, gyroscopes, magnetometers, and/or barometers (collectively, the set of accelerometers, gyroscopes, magnetometers, and/or barometers are called an inertial motion unit (IMU) 112 of FIG. 1, which are implemented on one or more semiconductor chips as are well known), and/or global-positioning sensors (GPS) which are optionally combined with an IMU, and the resulting system also implemented on one or more semiconductor chips, as are well known), a computing processor, a power source and a radio-communications device, (2) a human-user-interface device, such as a smart phone having one or more output devices such as a video display, speaker(s) or earphones, haptic outputs (e.g., vibration configured to be sensed by a human user) and/or electrical nerve-stimulation outputs, wherein the human-user-interface device includes a radio-communications device, a processor executing software of the invention, and user-interface (UI) input and output devices. Some embodiments further include wireless communications to a central server computer that also communicates to other users for the purposes of one-on-one and/or group competition, game play, self-improvement, training, etc. Some embodiments further include physiological sensors that sense such parameters of the user such as breathing, heart rate, blood-oxygen content, muscle electrical activity, and the like.

In some embodiments, the software of the invention includes mathematical routines interpreting the motion activities of a first human user such as running (speed and distance), bicycle speed (wheel rotation), and dynamic motion capture of bicycle-pedal angles and foot angles (relative to the ground) without external mechanical position synchronization. In some embodiments, the software of the invention also includes game routines configured to elicit and receive data based on the motion activities of the first human user and optionally motion activities of a plurality of other human users, game routines configured to generate one or more performance scores of the first user and optionally one or more performance scores of the plurality of other human users, game routines configured to gather performance scores and provide rankings and the like, and to provide formatted output of the performance scores. In some embodiments, the software generates visual output to each user that includes visible displays of graphical and/or color-coded continuous, near-instantaneous (real-time) indications of improvement or degradation of form, efficiency, performance, etc., and optionally short-term (e.g., one to five minutes) averages, workout averages, weekly, monthly or yearly averages, and changes to such parameters, and comparisons or relationships of such parameters to one or more other competitors in simultaneous competitions, or in competition with previous efforts of the current user or other users of the system. In other embodiments, the software additionally or alternatively generates audio output and/or haptic (e.g., vibratory) output to each user that indicates improvement or degradation of form, efficiency, performance, etc., and whether the user's competitors are catching up or being left behind. In some embodiments, the software receives GPS location data and corresponding terrain data, and combines the analysis of the user's physiological parameters with the predicted upcoming terrain (such as uphill or downhill slopes), and additionally or alternatively generates suggestions, such as for the user to, e.g., increase breathing rate to improve blood oxygen levels in anticipation of an upcoming uphill climb.

In some embodiments, the present invention provides an apparatus that includes: a portable personal electronic device that wirelessly receives data from a foot-mounted sensor module that includes at least two accelerometer sensors to provide acceleration measurements in at least two orthogonal directions and at least two gyroscope sensors to provide rotational or gyroscopic measurements around at least two orthogonal axial directions; a processor that calculates foot angles at a plurality of successive positions within each of a plurality of strides of a human user during an athletic activity; and an output device in the personal electronic device that presents human-perceptible indications based on the calculated foot-angle data. In some such embodiments, the calculated foot angles are used as inputs to a game or competition between or among two or more competitors, such as a competition to determine who may best improve their athletic form or efficiency at some activity, wherein the processor is used as a referee or score keeper to judge performance results. In some such embodiments, the processor is configured to receive or determine input signals from the competitors (via backpedaling, tapping on the brakes of the bicycle, or other input sensor(s)) to start or stop data collection during some portion of a workout or competition, in order to calculate and track a score or other performance metric based on measured foot angles, accelerations, tilting, and/or twisting during bicycle pedal strides or running steps within that portion of the workout or competition. In some embodiments, scores or other performance or form metrics are posted on a "leader board" that collects and ranks such metrics on a local, regional and/or national basis. In some embodiments, the analytics performed by the software of the present invention provides a level of validation on the metrics to prevent or reduce cheating. In some embodiments, the scores and/or other metrics are encrypted using blockchain technology that also includes additional other parameters that allow later re-analysis of the collected data in order that later-applied software analysis can identify and remove suspect scores or tampered data, to further reduce cheating and fraudulent achievement claims.

In some embodiments, data received from a plurality of sensor elements (such as three accelerometers, three gyroscopes, three magnetometers, a barometer pressure sensor, and/or a sound sensor), all embedded in a sensor module are correlated and analyzed, optionally also including data inputs received from the user such as (backpedaling, coasting, turning around while running, and the like) to provide dead-reckoning and sensor-drift compensation without the need for carrying a cell phone or other personal electronic device during the workout itself. Rather, in some embodiments, the athlete carries merely the foot-mounted sensor, which includes on-board storage for recording thousands or even hundreds of thousands of data values from each of the plurality of sensor elements, for the duration of a biking or running workout, and then uploads all of the data, after the workout, into their cell phone, laptop computer or other personal electronic device for analysis and posting onto a leader-board or other competition-tracking service. In some embodiments, the analyzed data results in generating scores and/or other metrics that are encrypted using blockchain technology (that optionally also includes additional other parameters into the blockchain data that allow later re-analysis of the collected data) in order that later-applied software analysis can identify, flag, and/or remove suspicious scores or tampered data, to further reduce cheating and fraudulent achievement claims.

Using the present invention, it has been discovered that pedaling, wheel spin, backpedaling, dithering, and coasting on a bicycle, and various aspects of running such as keeping on toes versus more flat-foot jogging, as well as spinning around or running backwards, and swimming activities all have unique motion signatures. In some embodiments, the system of the present invention is programmed to autodetect the activity (e.g., bicycling versus running versus swimming) and the various aspects or changes within the activity such that the user does not need to configure the system differently for each activity (by phone app, or device DIP switches, or the like). In some embodiments, the auto-detection functions make switching activity a lot easier. In some embodiments, the very same sensor is continuously carried by competitors in triathlon competitions that involve running, bicycling and swimming, and the sensors then upload the data recorded throughout the competition to enable analysis of whether the competitor did indeed complete the specified course, and also to allow comparisons of the form and performance of each competitor versus other competitors in the same race or in races run at different times and in different places, wherein in some embodiments, the comparisons and scores for various competitors and triathlons are posted or available for lookup. In some embodiments, the analysis of data for each triathlete is analyzed and presented to that user of the present invention in order that the user and/or their coach can compare and contrast various performance and form aspects of each activity for self-improvement purposes.

Another application of the present invention is to gather motion, angles, and other data from a manufacturing or medical environment to enable real-time or later analysis and presentation of results and process-improvement suggestions based on methods, movement, efficiency, neatness, or other aspects of a manufacturing process in a factory, or of a medical procedure in a hospital, doctor's office or ambulance.

The real magic about the present invention (for many users anyway) is that it can help the bike rider properly coordinate all the mechanical components of most efficient pedaling (hip, knee, ankle). Watching the real-time display of the present invention showing measured foot angles as compared to proper foot angles is like a video game where your actual body is the subject and object of the game.

In some other conventional settings, a bike fitter will record videos of the user's ride, and try to have software calculate the angles and distances for the relative placement of saddle set back and height, handlebar distance and drop, and pedal crank length, and the rider sees a resulting list of numbers, and the bike fitter changes the saddle height. For all kinds of reasons this is insufficient, ineffective and/or meaningless in terms of rider comfort and efficient riding. (See, e.g., the papers "Riding Motion Capture System Using Inertial Measurement Units with Contact Constraints" by Maruyama et al. and "The Need for Data-Driven Bike Fitting: Data Study of Subjective Expert Fitting" by Braeckevelt et al. (cited above) on how ridiculous it is to rely on videos and/or conventional bike-fitting professionals because of the large range of variable parameters recommended by different bike-fitting professionals for the same riders.)

Bike measurements are important, but at a certain point the rider is responsible for moving in the proper manner—something that is not necessarily even captured in the way one would expect. For example, kinesthesia, the awareness of the position and movement of the parts of the body by means of sensory organs (proprioceptors) in the muscles and joints can be beneficially supplemented by the electronic sensors and processing method of the present invention to display and present data relevant to knowledge of body angles set forth by the present invention. For one example: when one of the present inventors could not get his foot angles correct, that person looked away from the phone displaying output of the present invention and focused on recommended leg motion he had read about earlier, rather than foot angle. He found a subtle motion change that felt perfect. By accident, he looked down and suddenly the phone showed all his angles were perfect, which is something he would never have realized without the visual display of the present invention, and his bike riding changed forever at that moment.

Many point-of-sale bike stores no longer have people knowledgeable about fitting a bike to a customer or customer to a bike. Along with some simple tape-measured parameters, the present invention fine tunes some of the parameters and the customer could receive a printout or an email report on many aspects of their physical riding characteristics. Having that data means the user can have meaningful conversations with others. Important measured variables are the foot angles, hip rocking and torso rotation. We think real-time alerts (e.g., from a wristband or phone vibration) issued by the present invention when the user's technique starts to go wrong can help a rider when proper riding is most important—when they are tired as hell.

In contrast, merely mounting a sensor on the crank will show variations in velocity, something one wants to be constant.

The entire set of data from the present invention is of interest to the most serious riders and is something the device of the present invention can provide.

BRIEF DESCRIPTION OF THE DRAWINGS

A more complete understanding of the present invention may be derived by referring to the detailed description and claims when considered in connection with the figures, wherein like reference numbers refer to similar items throughout the figures.

Some embodiments of the present invention are illustrated as an example and are not limited by the figures of the accompanying drawings, in which like references may indicate similar elements and in which:

FIG. 3C is a graph 303 showing Gyro filtering effects on angle and amplitude, where plot 330 is filtered gyro angle and plot 340 is unfiltered gyro angle, according to some embodiments of the present invention.

DESCRIPTION OF PREFERRED EMBODIMENTS

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

System Components

Figure 1A:
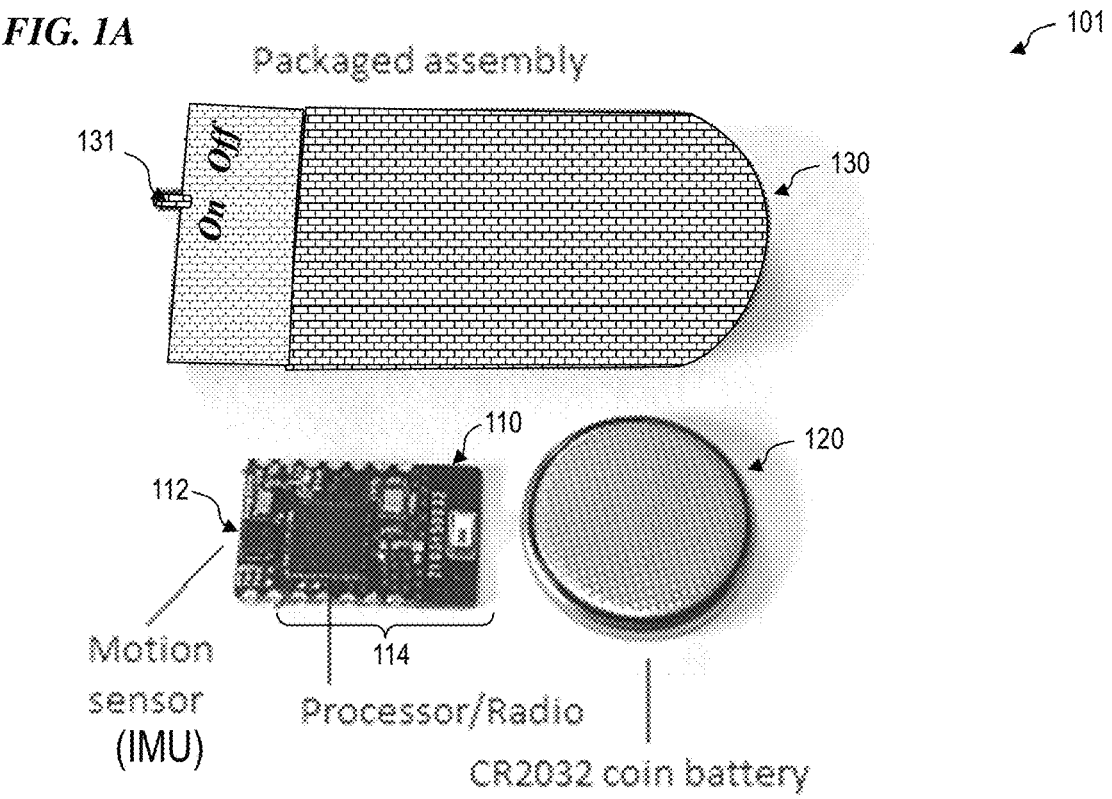
FIG. 1A is a photograph motion-sensor-and-transmitter system 101 that includes electronic circuit board 110 with motion sensor 112, and processing unit including an RF radio 114, a coin battery 120 and enclosure 130, according to some embodiments of the present invention.
Figure 7:
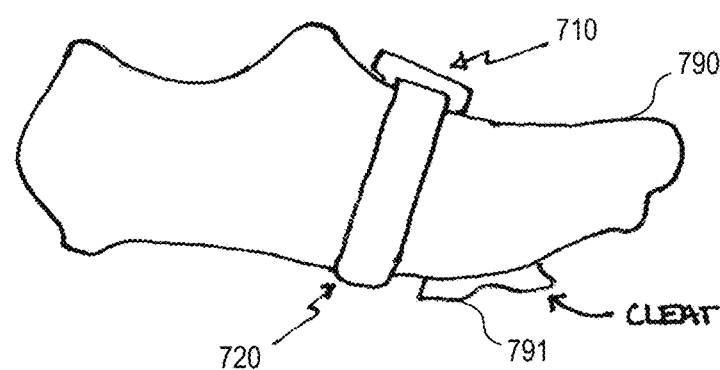
FIG. 7 is a side-view sketch 701 of a sensor 710 mounted on a bicycle shoe 790, according to some embodiments of the present invention.

FIG. 1A is a photograph of a motion-sensor-and-transmitter system 101 that includes electronic circuit board 110 with motion sensor 112, and processing unit including an RF radio 114, a coin battery 120 and enclosure 130, according to some embodiments of the present invention. In some embodiments, battery 120 is operatively coupled to provide electrical power to motion sensor 112 and processing unit including RF radio 114, and all of these are held in enclosure 130. In some embodiments, enclosure 130 is held to the top (or other portions) of the athlete user's shoe by a strap (as shown in FIG. 7), or by using Velcro®-type, snap or other suitable fastener.

In some embodiments, sensor 112 includes three accelerometers and three gyroscopes. In some embodiments, processing unit 114 includes non-volatile memory for executing programs that elicit and receive data from sensor 112, perform radio control and control application data storage. Motion data from sensor 112 is captured by processor 114, analyzed depending on the current use-scenario and/or stored locally and passed on to other devices using the radio interface. In some embodiments, sensor 112 is instructed to alter characteristics such as: sample rate (faster to improve accuracy or slower to run on phones with less compute power), data content, compression schemes, application analysis, radio communication protocols, etc.

The other system components are the part(s) in which data analytics are performed, for example, as software executed in a smart phone carried by the athlete user, which are described in the next sections of this document.

In some embodiments, data-analysis functions include pedal monitoring (such as cadence, pedal angle). In some embodiments, cadence (in some embodiments, denoted as pedal strokes per minute) is determined by two digital-filter algorithms that operate on the received accelerometer vertical-axis data. In some embodiments, the first low-pass filter (around 3 Hz) reduces mechanical noise and the second low-pass filter (around 0.5 Hz) is used as a base-line average; removing errors due to DC-offset, sensor drift, and road-level-variation signals. As the pedal cycle crosses the baseline in the positive and negative direction, that indicates one rotation of the mechanical crank arm. (The accelerometer amplitude is checked to ensure there was proper rotation, rather than only stationary angling of the pedal.)

Figure 1B:
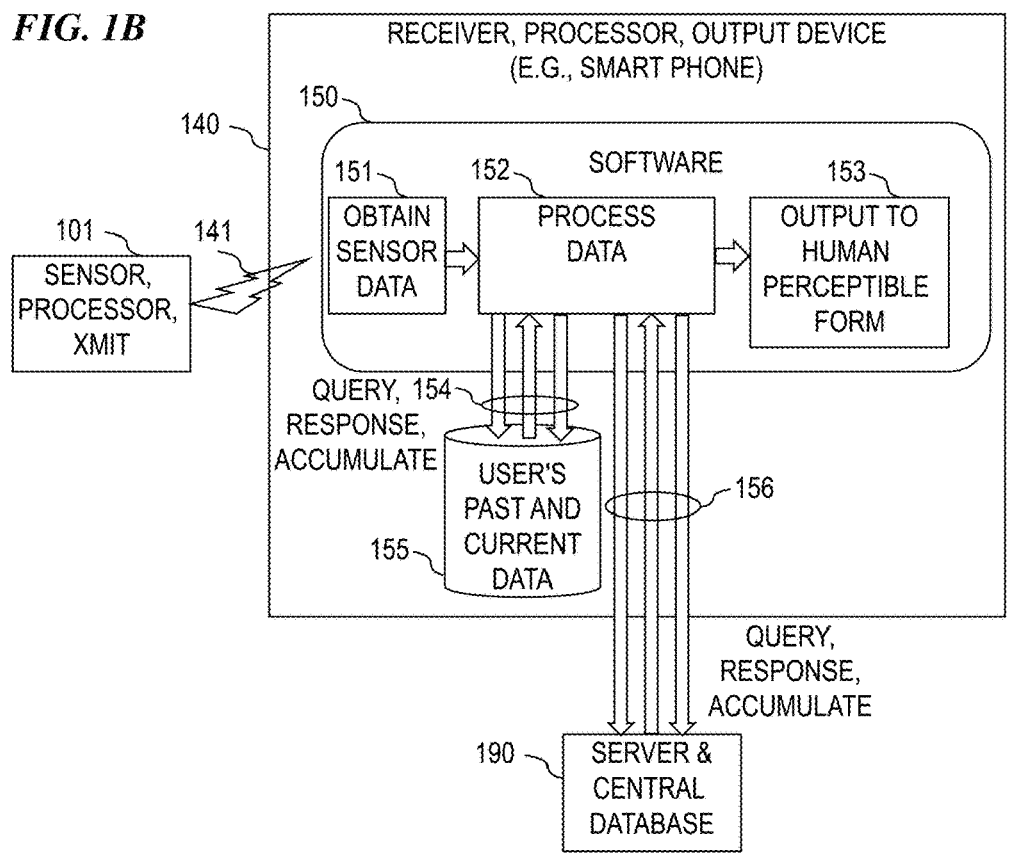
FIG. 1B is a block diagram of a system 102, according to some embodiments of the present invention.

FIG. 1B is a block diagram of a system 102, according to some embodiments of the present invention. In some embodiments, system 102 includes one or more motion-sensor-and-transmitter systems 101, each of which wirelessly transmits sensor data 141 based on its sensed data to receiver-processor-output system 140 (in some embodiments, a smart cell phone). In some embodiments, system 140 includes a memory that stores software 150 that is executed by system 140. In some embodiments, software 150 includes sensor-data module 151 that elicits and receives sensor data 141, data-analysis module 152 that processes the received sensor data along with other data (e.g., processing parameters and past data regarding past performance of the human user and/or other users) elicited and received from local storage 155, and output module 153 that is used to format and control presentation of the processed sensed data. In some embodiments, the output data is visual data presented on a display (e.g., a video display of the smart phone), audio data that is output from a speaker or earphones, and/or haptic data (such as vibrations from a weight rotated by a small motor) that is used to motivate, train or entertain the user athlete. In some embodiments, processor module 152 elicits and receives 154 data (such as the user's past and current performance-efficiency and performance-form data) from local storage 155, and outputs formatted data to local storage 155. In some embodiments, processor module 152 also elicits and receives 156 data (such as the user's past and current performance-efficiency and performance-form data) from a "central" computer server and storage 190, and outputs formatted data to computer server storage 190. In some embodiments, "central" computer server and storage 190 is used by the user of system 140 and also by similar systems of other human users.

Figure 1C:
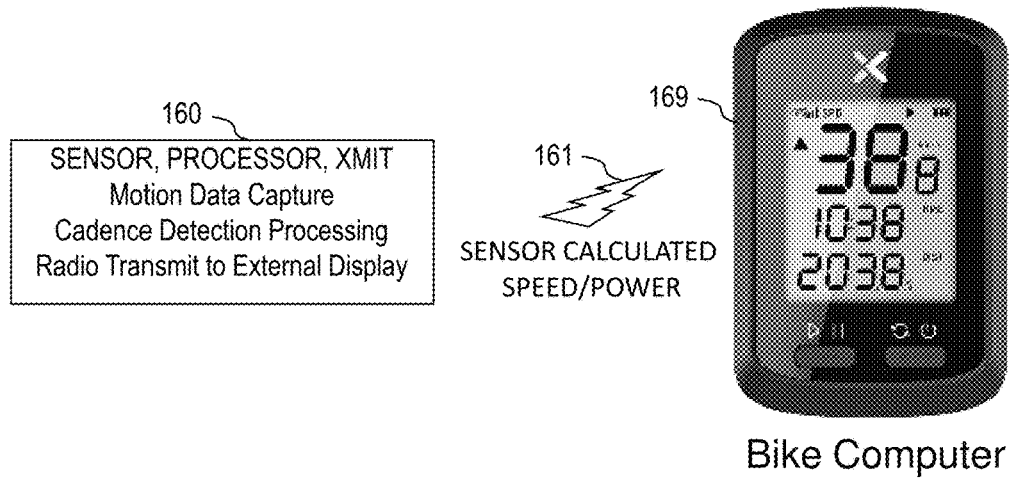
FIG. 1C is a block diagram of a system 103, according to some embodiments of the present invention.

FIG. 1C is a block diagram of a system 103, according to some embodiments of the present invention. In some embodiments, system 103 includes a high-function sensor-processor-transmitter system 160 that combines most of the sensing performed by system 101, as well as the processing performed by software processing 152 shown in FIG. 1B and described above, and that outputs highly processed output data 161 that is wirelessly transmitted to a separate output device such as bike computer 169, for display and/or audio output. In some embodiments, sensor-processor-transmitter system 160 performs the majority of processing needed for the sensed data.

Figure 1D:
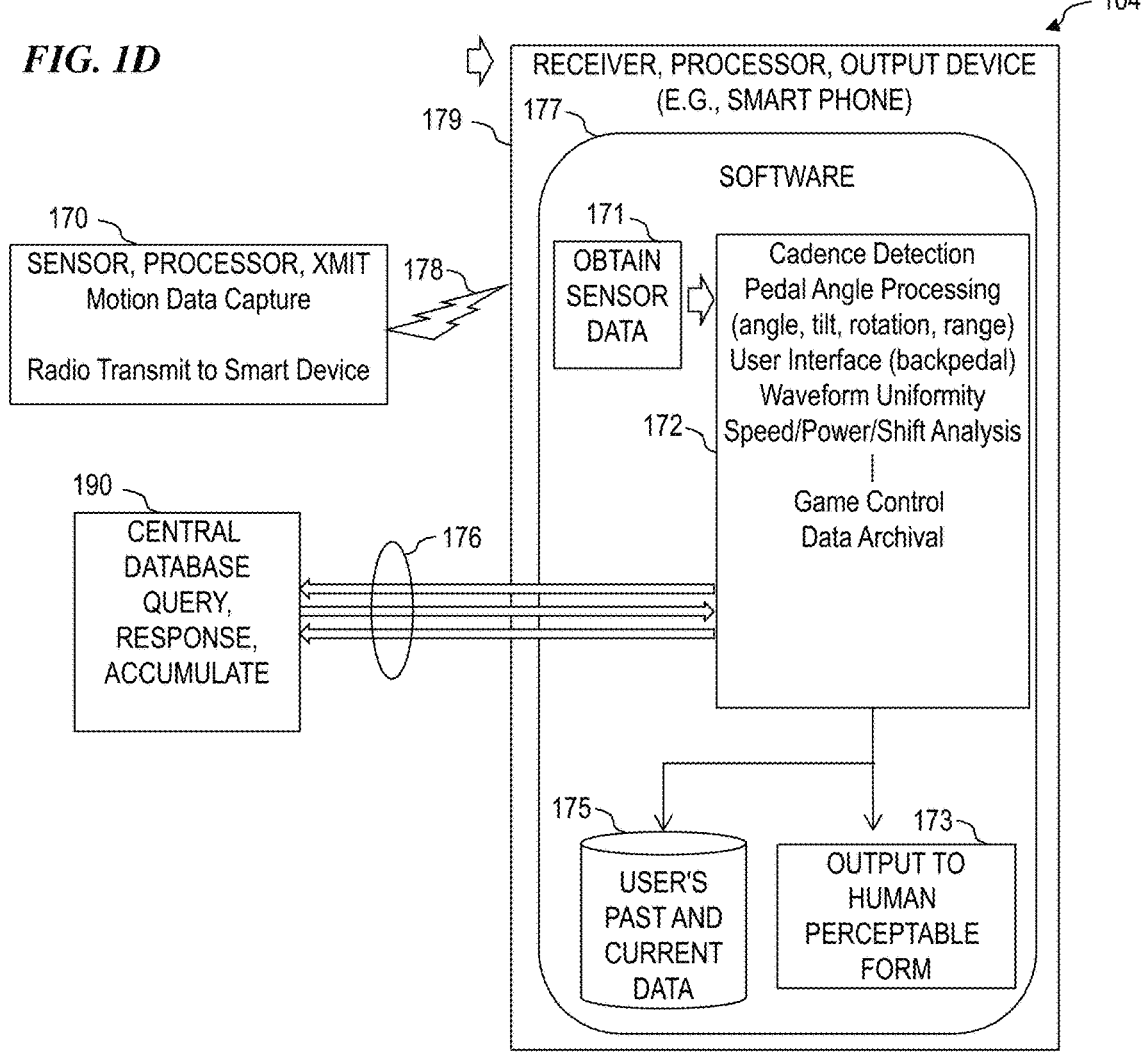
FIG. 1D is a block diagram of a system 104, according to some embodiments of the present invention.

FIG. 1D is a block diagram of a system 104, according to some embodiments of the present invention. In some embodiments, system 104 includes a minimal-function sensor-processor-transmitter system 170 that performs most of the sensing performed by system 101, and that outputs minimally processed output data 178 that is wirelessly transmitted to a separate output device such as smart phone 179, for display, audio and/or haptic output. In some embodiments, system 140 includes a memory that stores software 150 that is executed by system 140. In some embodiments, software 177 in smart phone 179 includes sensor-data module 171 that elicits and receives sensor data 178, data-analysis module 172 that processes the received sensor data along with other data (e.g., processing parameters and past data regarding past performance of the human user and/or other users) elicited and received from local storage 175, and output module 173 that is used to format and control presentation of the processed sensed data. In some embodiments, the output data is visual data presented on a display (e.g., a video display of the smart phone), audio data that is output from a speaker or earphones, and/or haptic data (such as vibrations from a weight rotated by a small motor) that is used to motivate, train or entertain the user athlete. In some embodiments, processor module 172 elicits and receives data (such as the user's past and current performance-efficiency and performance-form data) from local storage 175, and outputs formatted data to local storage 175. In some embodiments, processor module 172 also elicits and receives 176 data (such as the user's past and current performance-efficiency and performance-form data) from "central" computer server and storage 190, and outputs formatted data to computer server storage 190. In some embodiments, "central" computer server and storage 190 is used by the user of system 179 and also by similar systems of other human users.

Figure 1E:
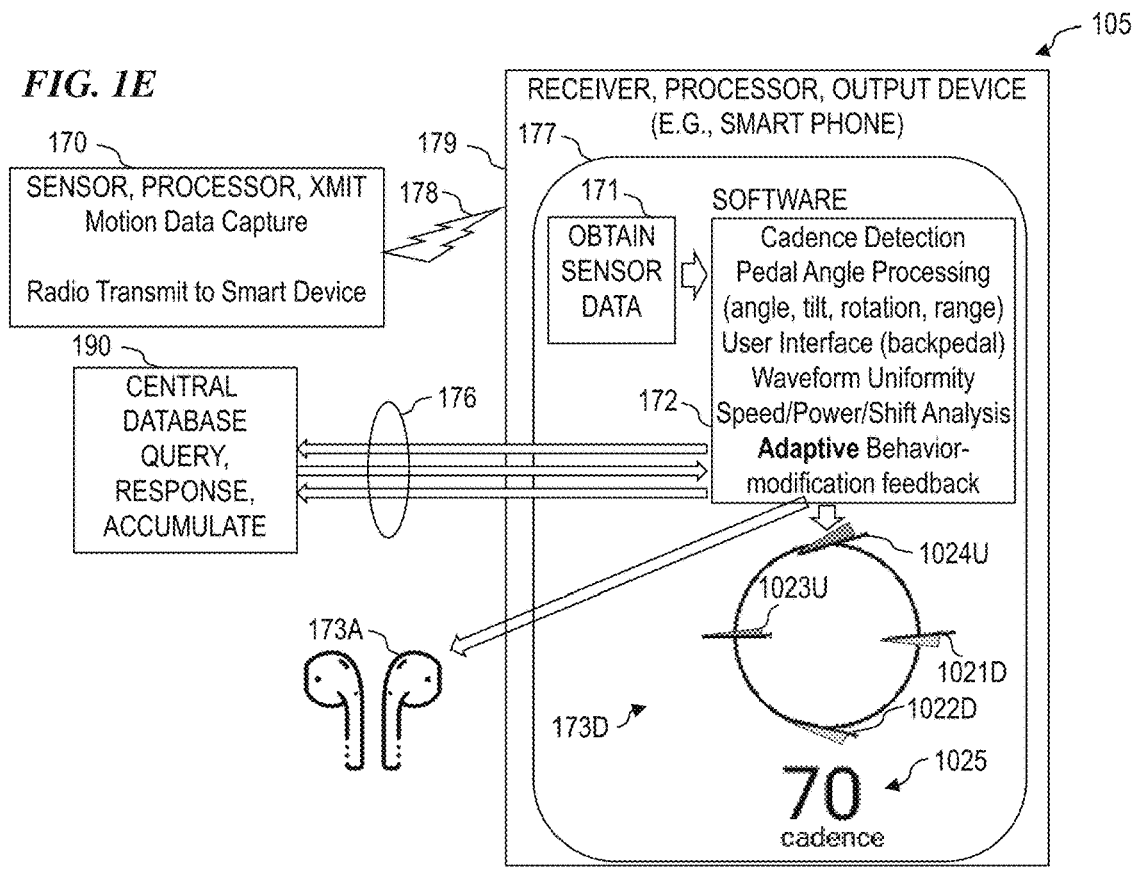
FIG. 1E is a block diagram of a system 105, according to some embodiments of the present invention.

FIG. 1E is a block diagram of a system 105, according to some embodiments of the present invention. In some embodiments, system 105 is substantially similar to system 104, with additional functionality of both visual output display 173D (such as four foot angles and angular differences and directions of each foot angle to a desired or ideal foot angle, wherein the reference numbers 1021D, 1022D, 1023U, 1024U and 1025 are explained more fully below in reference to FIG. 10B) and audio output device(s) 173A, such as wireless earbuds or the like.

In some embodiments, the visual output display 173D and/or audio output device(s) 173A provide clear, continuous and substantially instantaneous indications to the user of the angles of their foot and/or how much and in which direction to try to change the foot angles at each of a plurality of positions. In some embodiments, this data is continuously updated and compiled for the entirety of a workout, to provide information as to the angles at each of a plurality of positions, the variation of each angle across a range of time (such as illustrated in FIG. 17B and FIG. 17C), and/or a comparison among a plurality of competitors in real time and/or for compilation and updates to an internet-hosted "leader board" of competitors.

Figure 2:
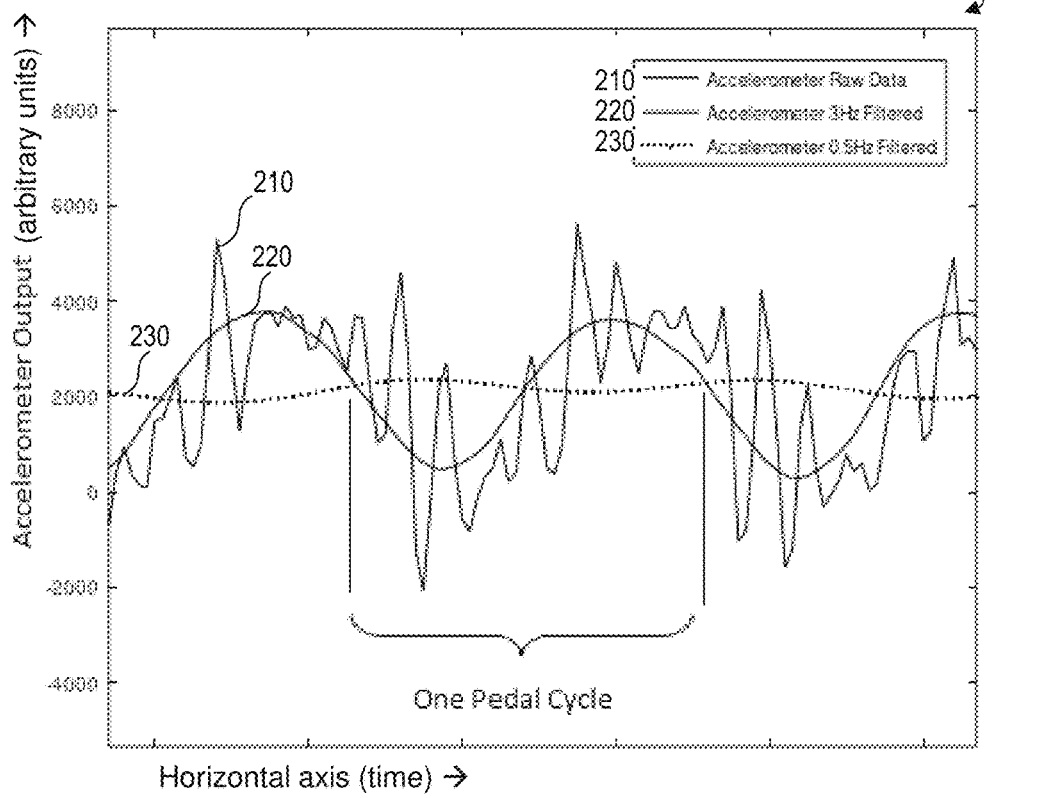
FIG. 2 is a graph 201 of accelerometer data 210 versus time, obtained from a vertical-axis accelerometer detecting one pedal cycle 220, according to some embodiments of the present invention.

FIG. 2 is a graph 201 of accelerometer data 210 versus time, obtained from a vertical-axis accelerometer detecting one pedal cycle 220, according to some embodiments of the present invention.

Cycles per Minute=60 seconds/(number of samples*sample time)

At a sensor-sample rate of 50 Hz, the time period is 20 milliseconds. If the one pedal cycle takes 40 samples, then cadence=60/(40*0.02)=75 pedal cycles per minute (PCPM).

In some embodiments, Pedal Angle Forward facing pedal angle pitch is determined by measuring gravity at the vertical (az) and fore/aft (ax) accelerometers using the formula: angle (degrees)=atan(ax/az)*57.296. Unfortunately, the rotating pedal influences the accelerometers (the same as gravity), and mathematically removing the circumferential signal can be prohibitively complex. Another method of determining pedal angle is with a gyroscope (which is unaffected by gravity and acceleration that does not include an angular component), but gyroscopes are subject to significant drift. In some embodiments, the present invention uses its novel method of determining rotating pedal angle that uses the combination of a gyroscope data (without drift), and angle-correction from accelerometers (after removing circular forces).

Pedal Angle=Gyro(filtered)+Accelerometer Angle (excluding rotation vector)−Sensor Mount Angle.

Figure 3A:
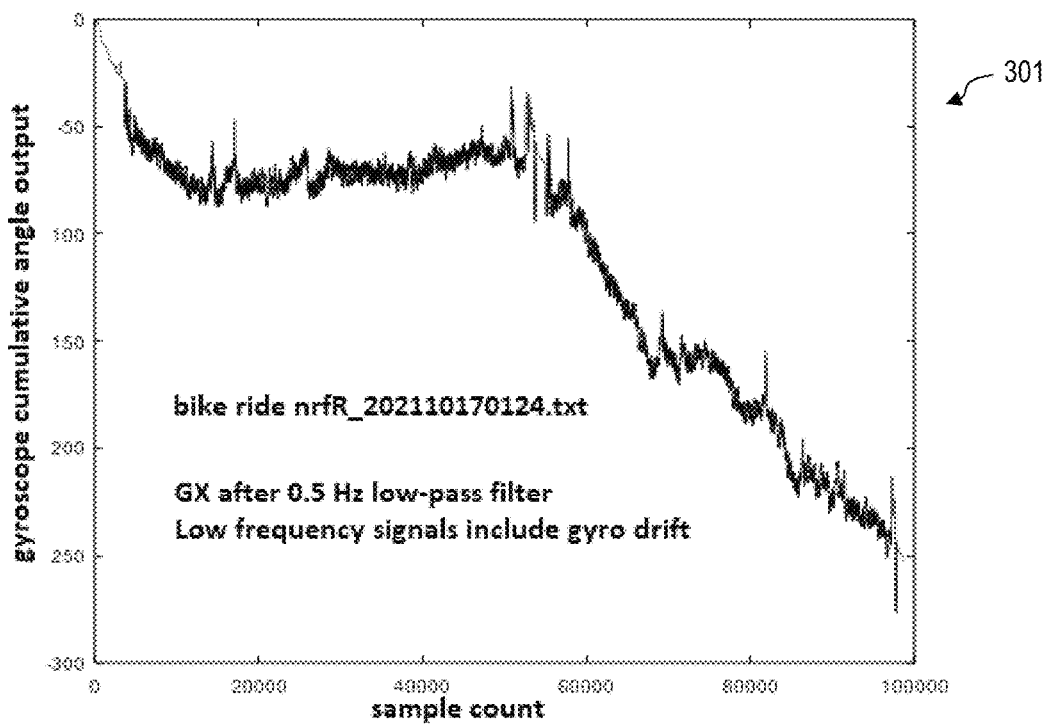
FIG. 3A is a graph 301 of the forward pedal angle gyro data filtered at 0.5 Hz, according to some embodiments of the present invention.

FIG. 3A is a graph 301 of the Gyro data low-pass filtered at 0.5 Hz. This reveals slow frequencies such as Gyro drift. Typically, gyroscopes are calibrated at the beginning of each use, and the stationary drift is compensated at each sample. Once the gyro is in motion, however, this drift factor changes, as seen in this graph.

Figure 3B:
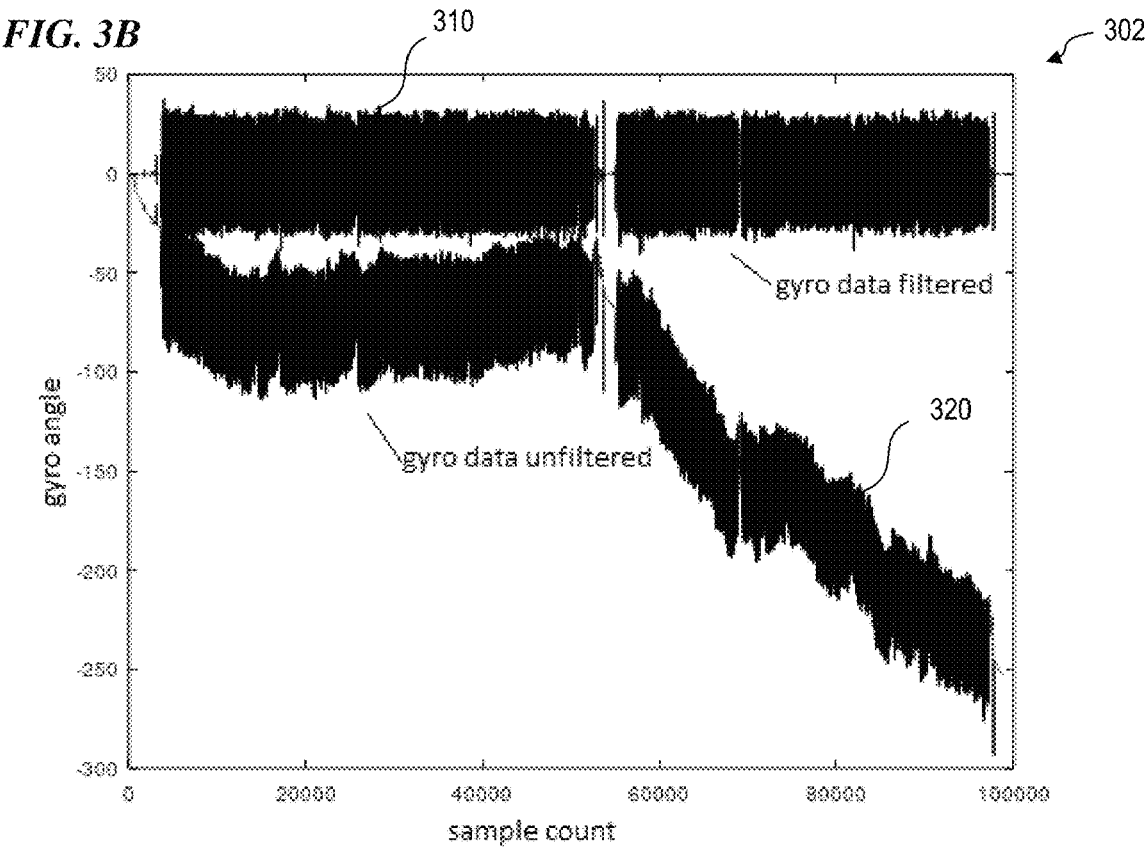
FIG. 3B is a graph 302 of Gyro drift removal filtering showing unfiltered gyro data 320 and filtered gyro data 310, according to some embodiments of the present invention.

FIG. 3B is a graph 302 of Gyro drift removal filtering showing unfiltered gyro data 320 and filtered gyro data 310, according to some embodiments of the present invention. FIG. 3B shows the pedal angle gyro signal during a 10-mile trail ride that includes a 200-foot incline. The first half was five (5) miles up-hill and then a return—with a down-hill increase in cadence (causing more gyro signal drift). Filtering out the slow-changing signals removes the drift signal as well as subtle angle changes in the trail surface.

FIG. 3C is a graph 401 showing Gyro filtering effects on angle and amplitude, where plot 330 is filtered gyro angle and plot 340 is unfiltered gyro angle, according to some embodiments of the present invention. FIG. 3C shows a single gyroscope cycle comparing un/filtered signals. Through the entire bike ride, the two phase signals remain identical. Comparing this cycle peak/valley amplitude shows a relatively insignificant amplitude change of 1.3% due to signal filtering.

Figure 4:
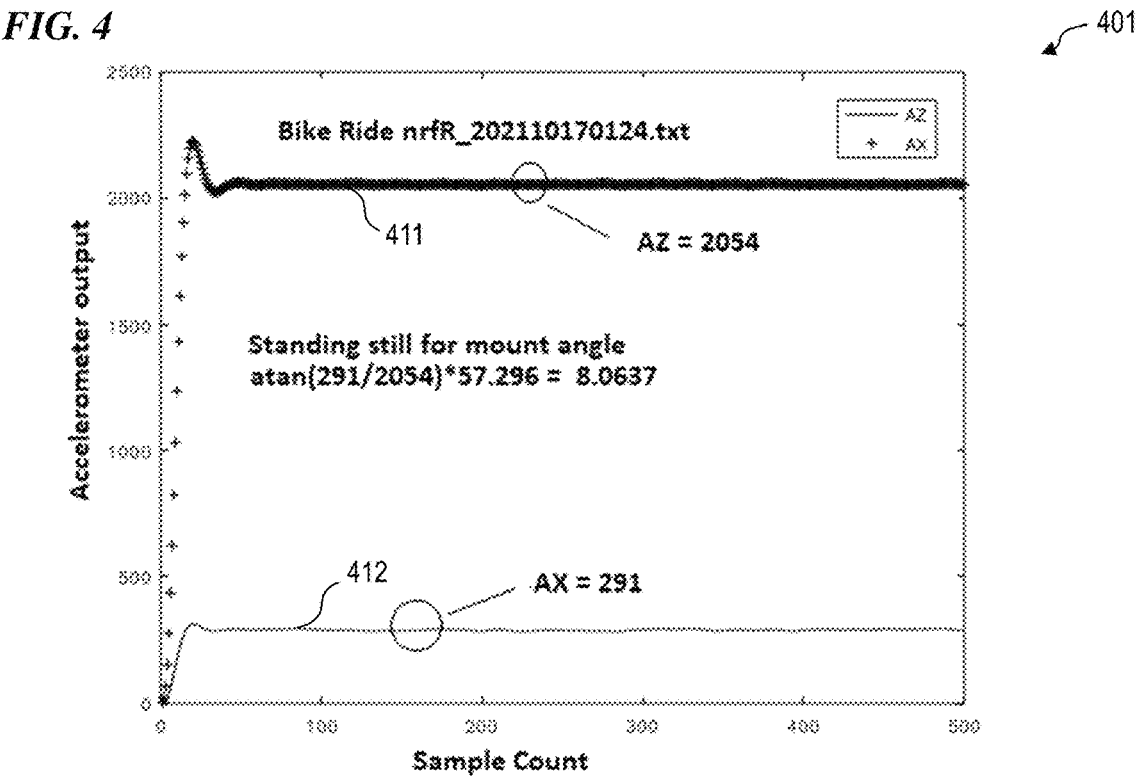
FIG. 4 is a graph 401 showing plots of acceleration 411 in the Z direction and acceleration 421 in the X direction during a pre-ride calibration of sensor module orientation on the user's foot, which is performed at the beginning of each ride, according to some embodiments of the present invention.

FIG. 4 is a graph 401 showing plots of acceleration 411 in the Z direction and acceleration 421 in the X direction during a pre-ride calibration of sensor module orientation on the user's foot, which is performed at the beginning of each ride, according to some embodiments of the present invention.

Figure 5:
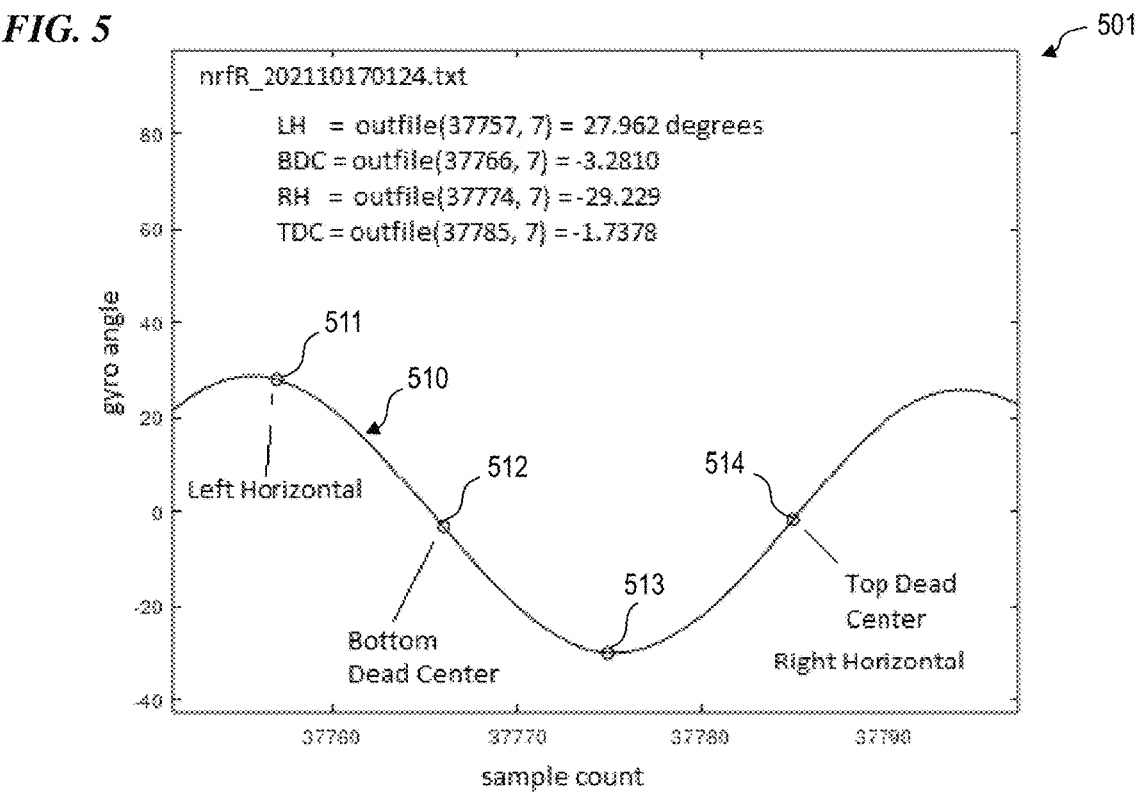
FIG. 5 is a graph 501 showing foot/Gyro-Location Angle, according to some embodiments of the present invention.

FIG. 5 is a graph 501 showing foot/Gyro Location Angle, according to some embodiments of the present invention. FIG. 5 shows using vertical (az) accelerometer to determine the pedal data sample-point for Top Dead Center (az minimum) and Bottom Dead Center (az maximum). On equal sides of these two locations are the Left Horizontal and Right Horizontal pedal locations. The gyro angles at these locations are saved.

Figure 6:
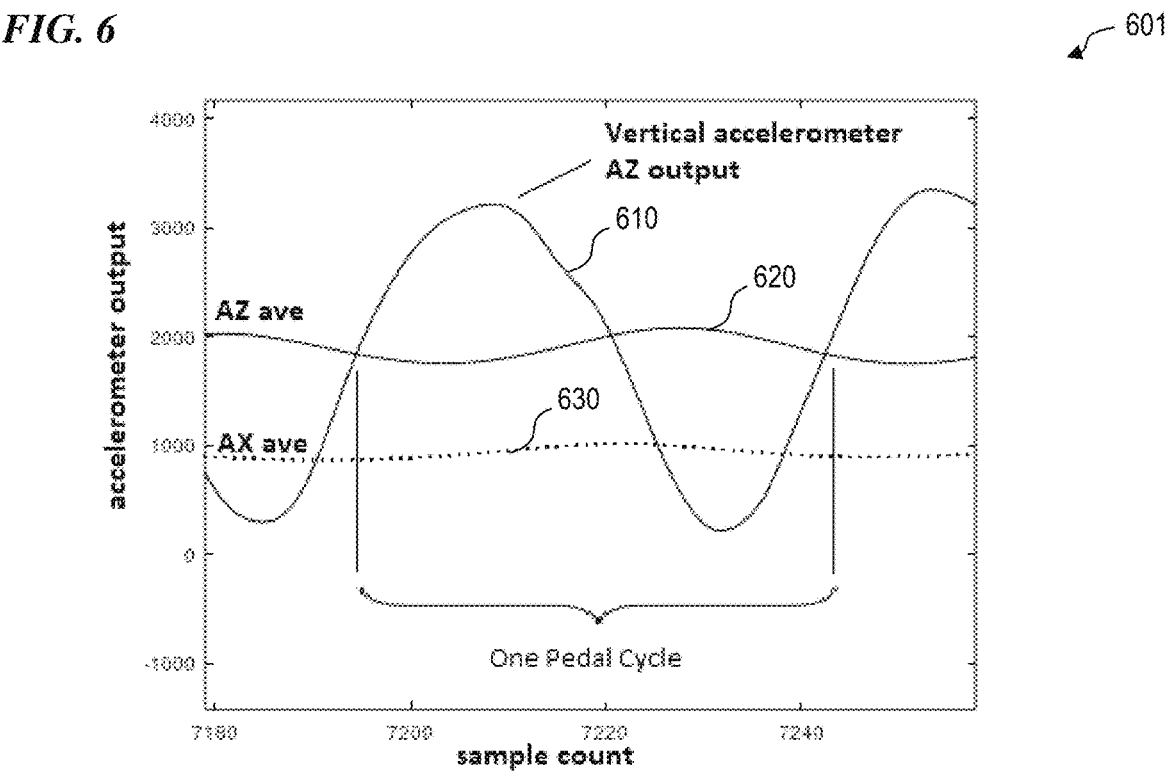
FIG. 6 is a graph 601 showing pedal Average Angle minus Circular Signal, according to some embodiments of the present invention.

FIG. 6 is a graph 601 showing pedal Average Angle minus Circular Signal, according to some embodiments of the present invention. Since the bicycle rider's foot returns roughly to the same pedal cycle starting angle, the sum of accelerometer signals will cancel out the positive/negative signals added to by the rotating crank arm. Signal averages can be used to determine the rider's individual pedal-cycle average angle. This accelerometer average angle is then added to the foot/gyro location angle calculated from an arctangent: atan(AX/AZ)*57.296=26.286098

FIG. 7 is a side-view sketch 701 of a sensor 710 mounted on a bicycle shoe 790, according to some embodiments of the present invention. In FIG. 7, the sensor 710 is held to the user's shoe with a strap 720, where, in FIG. 7, the shoe is not necessarily representing the foot along the horizontal plane. In some embodiments, at the beginning of the ride, the cyclist stands still on a flat surface for the first few seconds of operation of the system of the present invention (such as, allowing the system to use data elicited and received from the accelerometers to determine the sensor mounting angle. (In some embodiments, the system of the present invention determines foot angle and outputs a representation of foot angle in real time, (graphically represented as a sloped line for each of a plurality of angular positions around a circle representing one pedal stride, each of which optionally is rendered with a color (i.e., hue, saturation and/or intensity) indicative of how close to an ideal form is each position of the stride, for example, in some embodiments, a difference between the measured angle and some "ideal" angle is represented by different colors to provide reinforcement of correct behavior and) for example, to a display device. Real-time display of measured angle helps the rider adjust the sensor position to an optimal level position on the shoe.)

In this data set, the mount angle=8.059763 degrees (in some embodiments, rounded to 8.1 degrees).

Angle correction factor for this pedal stroke is: 26.3 (pedal angle)–8.1 (mount angle)=+18.2 degrees.

Figure 8A:
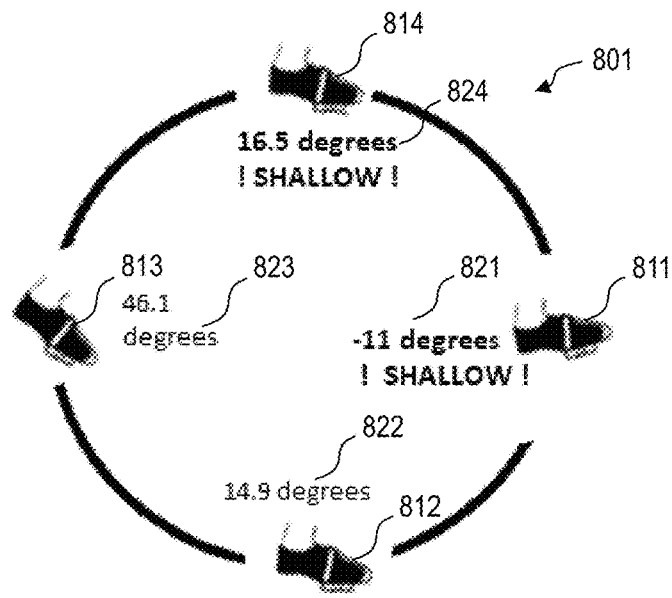
FIG. 8A is a side-view diagram 801 of a bicycle rider's foot angles at four angular positions during a single rotation cycle based on a Final Pedal Angle Calculation, according to some embodiments of the present invention.

Four final single-pedal-stroke-calculated foot angles of one stride (using FIG. 5 angles+corrections) are shown in FIG. 8A, where the four angular positions are used in this embodiment are: top dead center (TDC or 12-o'clock) position, the right-hand (RH or 3-o'clock) position in FIG. 8A, (90 degrees from TDC along the front side, downward stroke), bottom dead center (BDC or 6-o'clock) position, and the left-hand (LH or 9-o'clock) position in FIG. 8A, (90 degrees from BDC along the back side, upward stroke):

TDC=–1.7+18.2=16.5 degrees,
RH=–29.2+18.2=–11 degrees,
BDC=–3.3+18.2=14.9 degrees, and
LH=28+18.2=46.2 degrees FIG. 8A is a side-view diagram 801 of a bicycle rider's foot angles at four angular positions (12-o'clock, 3-o'clock, 6-o'clock and 9-o'clock) during a single rotation cycle based on a Final Pedal Angle Calculation, according to some embodiments of the present invention. In other embodiments, a greater number (e.g., five, or six (in some embodiments, 12-o'clock, 2-o'clock, 4-o'clock, 6-o'clock, 8-o'clock and 10-o'clock), or seven or eight, or more position angles) or a smaller number of position angles are calculated per stride. In some embodiments, where foot angles are measured at fewer than four positions per stride, or where measurements are made at different positions, and corresponding foot angles are calculated in successive strides, and a spline function is used to interpolate intermediate foot angles. In some embodiments, a calculated interpretation of the user's foot angle at one or more locations is performed and optionally presented to the human user (the bicyclist), wherein the data presented optionally includes such system-determined interpretation results, as shown as an example in FIG. 8A, that the foot angle of 16.5 degrees at the 12-o'clock TDC is "shallow" and the foot angle of –11 degrees at the 3-o'clock position during the downward stroke is "shallow", where additional behavior-modification information such as one or more exclamation mark(s) (as shown) or color encoding (such as an intensity, saturation and/or hue of a color), or a frequency of flashing of the display, that indicates of the interpretation are optionally included depending on the magnitude of the difference between the measured angle and some predetermined "ideal" or "desired" angle. In some embodiments, a color-coded presentation is displayed that indicates to the user as to whether they improving (moving towards an ideal angle, at each of one or more of the o'clock measurement positions) or not. In some embodiments, the presentation of the deviation-from-ideal interpretations modified or tempered so as to best provide behavior-improvement interpretation information while not disturbing the rider's overall performance. In some embodiments, the data are minimized in terms of how many of the o'clock positions are indicated as different from ideal in order that the user can concentrate on improving one "o-clock" portion of each stride without being discouraged that other "o-clock" portions of each stride may temporarily be interpreted as getting worse.

In some embodiments, the interpretation information is also or alternatively presented as audio output of the system of the present invention, either as text-to-voice converted encouragement, or as pitch or notes of a musical beat at the different positions of each stride so the human user can "tune" their athletic form to a desired pattern of foot angles at each of a plurality of o'clock positions in each stride. In some embodiments, individual left-and-right foot angle indications are presented in stereo earbuds or headphone speakers in the bicyclist's helmet, for example such that interpretations of left-foot form, effectiveness and/or changes toward and away from ideal are presented to the bicyclist's left ear and interpretations of right-foot form, effectiveness and/or changes toward and away from ideal are presented to the bicyclist's right ear.

In some embodiments, the interpretation of the user's form is compared to that of other bicyclists, either as individual competitors who are trying to see who can be best or most improved, or as a team that is competing against other teams of bicyclists. In some embodiments, the competition and relative differences to ideal form or relative improvements to form are presented visually and/or audibly to the competitors and/or members of teams. In some embodiments, the game progress and user-to-user data are transmitted and aggregated at a central server computer system or a distributed system in order to rank each user's performance, improvement, best scores and similar game-relevant information. In some embodiments, the aggregated information is evaluated and rewards (such as monetary rewards, non-fungible tokens (NFTs), publicity, and the like) are distributed.

In some embodiments, the stride data for each competitor on each competitive ride is checked for validity by system software of the present invention (such as validating strides, times of coasting or backpedaling, strides at correspond to the various terrains at GPS locations recorded by the user's cellphones on routes traveled during a ride and the like) and the validated data for each ride in the competition is encoded with blockchain data, and recorded in distributed systems as are well known for cryptocurrencies to ensure data integrity and validate that rides are not manipulated by unscrupulous competitors.

Figure 8B:
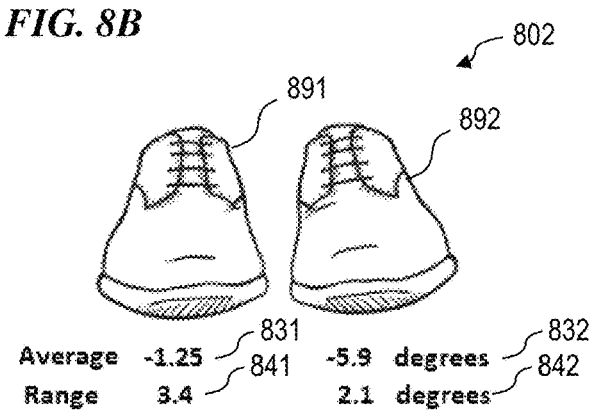
FIG. 8B is a front-view diagram 802 of a bicycle rider's foot average tilt angle positions and total range during an entire cycling ride.
Figure 8C:
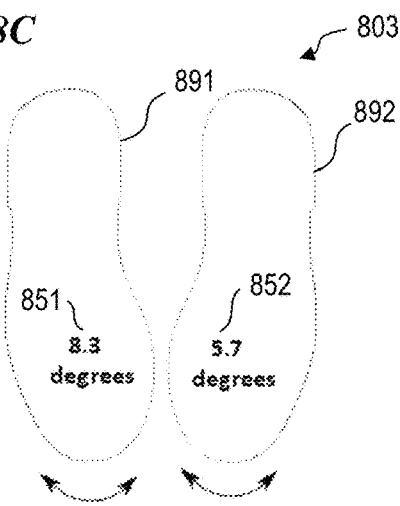
FIG. 8C is a bottom-view diagram 803 of a bicycle rider's foot total rotation angles during an entire cycling ride.

FIG. 8B is a front-view diagram 802 of a bicycle rider's foot measured average tilt-angles and total range during an entire cycling ride. In the embodiment shown, the right foot 891 has an average tilt angle 831 of –1.25 degrees and a range 841 of 3.4 degrees, and the left foot 892 has an average tilt angle 832 of –5.9 degrees and a range 842 of 2.1 degrees. In some embodiments, the tilt are measured periodically during a ride and optionally are presented FIG. 8C is a bottom-view diagram 803 of a bicycle rider's foot total rotation angles during an entire cycling ride. In the embodiment shown, the right foot 891 has an average rotation angle 851 of 8.3 degrees, and the left foot 892 has an average rotation 852 of 5.7 degrees.

Note: foot tilt and rotation are greatly affected by bicycle motions weaving and left-to-right rocking (sometimes called "wonking"—throwing every ounce of leverage, weight and power to the pedals). For this reason, bike fitting and adjustments are done with data collected while riding on a stationary bicycle (with minimal rider weaving and wonking). During normal riding these signals can be used in identifying rider activity (such as final-sprint wonking) and inefficient riding technique (such as weaving back-and-forth on a zig-zig path, rather than having the bicycle's wheels travel along a more-straight (shorter) line).

Figure 8D:
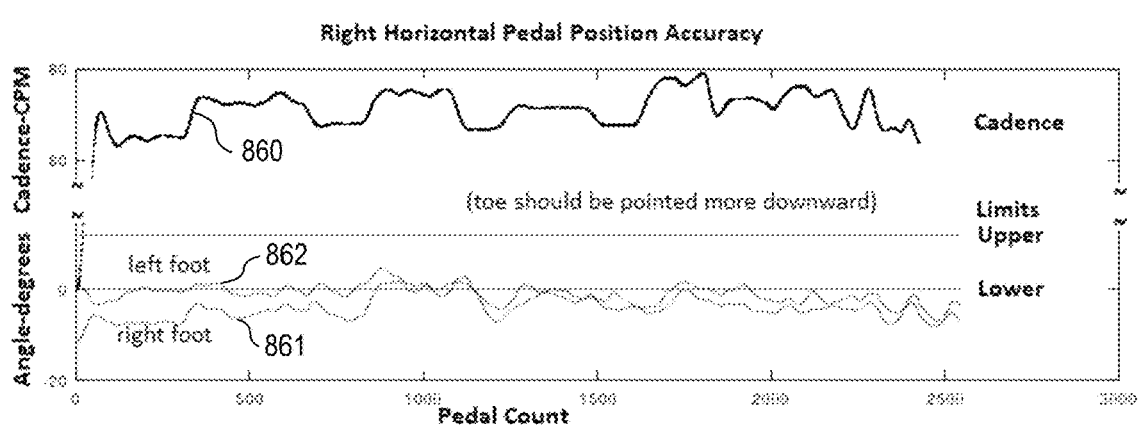
FIG. 8D is a chart showing one pedal location as measured during an entire cycling ride. Upper and lower limit lines show when the pedal compares to recommended position angles. Pedaling cadence for the entire ride is also shown.

FIG. 8D is a chart showing each pedal's location (862 for the user's left foot and 861 for the user's right foot) as measured during an entire cycling ride (where the horizontal axis is measured as pedal count). Upper and lower limit lines show when the pedal compares favorably to recommended position angles. For some bicyclist, the data in this graph may indicate that the user's toe should be pointed more downward. In some embodiments, this interpretation of form is presented visually and/or audibly to the user during the ride, in order that the user may try to improve performance or form, and/or presented to other competitors or team mates as a basis for competition and/or coaching. In some embodiments, pedaling cadence 860 as calculated in cycles per minute (CPM) for the entire ride is also shown.

Foot Monitoring (Foot Tilt and Rotation, Foot Motion Waveform, Back-Pedal Detection)

Foot Tilt and Rotation—Just as with pedal forward angle detection (pitch), the same technique can be used to measure foot side-to-side angles (roll). The gyro can also track foot rotation (yaw). Foot tilt and rotation are important elements for cycling efficiency as well as identifying causes of discomfort and injury. Bike fitters and physical therapists will often consider these measures in helping riders. Run-time analysis can detect abnormal conditions that will result in pain or injury later in the bike ride. By vibration, the phone can signal the rider that a change in pedaling motion is needed to avoid problems before they occur.

Foot-Motion Waveform—Foot motion throughout the pedal cycle can be an area of interest for improving bicycle performance. In some embodiments, the system of the present invention determines a waveform score, which, in some embodiments, is a value of between zero and one hundred (e.g., for example, a number representing a standard deviation of the rider's waveform compared to the ideal waveform). One example of an ideal pedal waveform is a sine wave. Waveform analysis could be used to identify problem areas of the pedal known as "dead spots", where angle and motion need to be improved.

Figure 9A:
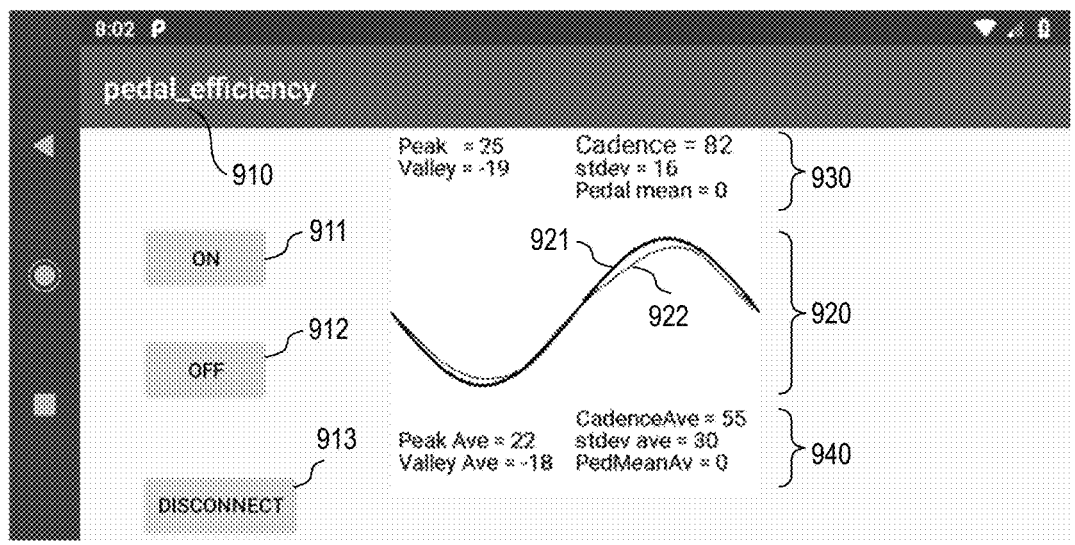
FIG. 9A is a screen shot 901 from a Pedal-Waveform Game, according to some embodiments of the present invention.

FIG. 9A is a screen shot 901 from a Pedal-Waveform Game, according to some embodiments of the present invention.

Figure 9B:
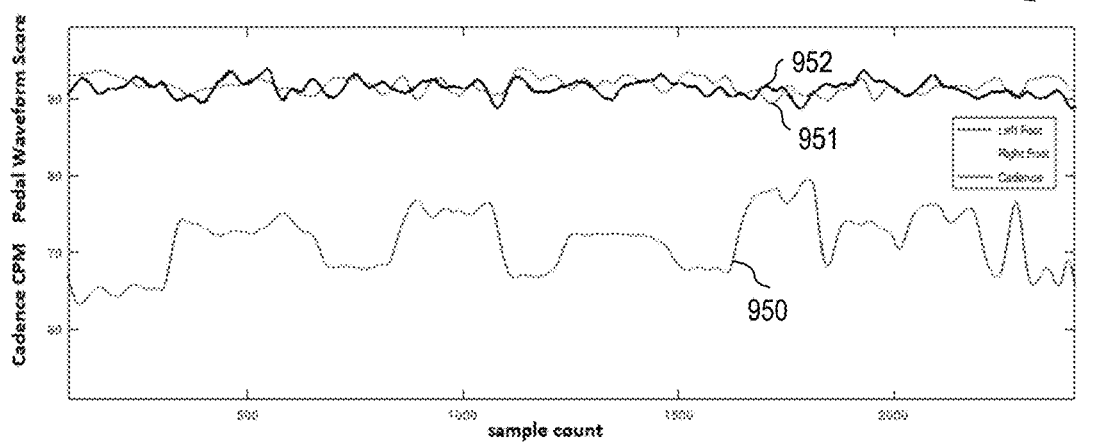
FIG. 9B is a graph 902 showing left and right pedal motion smoothness. The graph also shows the pedaling cadence.

FIG. 9B is a graph showing left and right pedal motion smoothness. The graph also shows the pedaling cadence.

Back-Pedal Detection

In some embodiments, pedaling backwards is detected as a means of hands-free control for functionality of the system software. For example, in some embodiments, an initial single instance of pedaling backwards is interpreted by the system software that the user wishes to start a period-of-time or interval of riding during which competitive form measurement is to be recorded and/or averaged, and a later-in-time single instance of pedaling backwards is interpreted by the system software as the time to stop the measurement interval. In some embodiments, two or three closely spaced back pedaling interspersed with coasting or forward pedaling is interpreted by the system software to indicate other aspects of game play such as a "time out" or "I'm not feeling well" or "I just got a cramp" or other such game-relevant signaling.

Standing or Off-Saddle detection—similarly, in some embodiments, whether the bicyclist is standing on the pedals (e.g., with one foot at 3 o'clock and the other at 9 o'clock to indicate a first signal to the system to initiate or terminate some "first" function, or one foot at 12 o'clock and the other at 6 o'clock to indicate a second signal to the system to initiate or terminate some "second" function. Examples of such functions include indicating to the system or other competitors or team mates whether the rider is tired or "pumped up", or feeling well or discouraged, or to initiate or end some game or competition function of the game.

Figure 15:
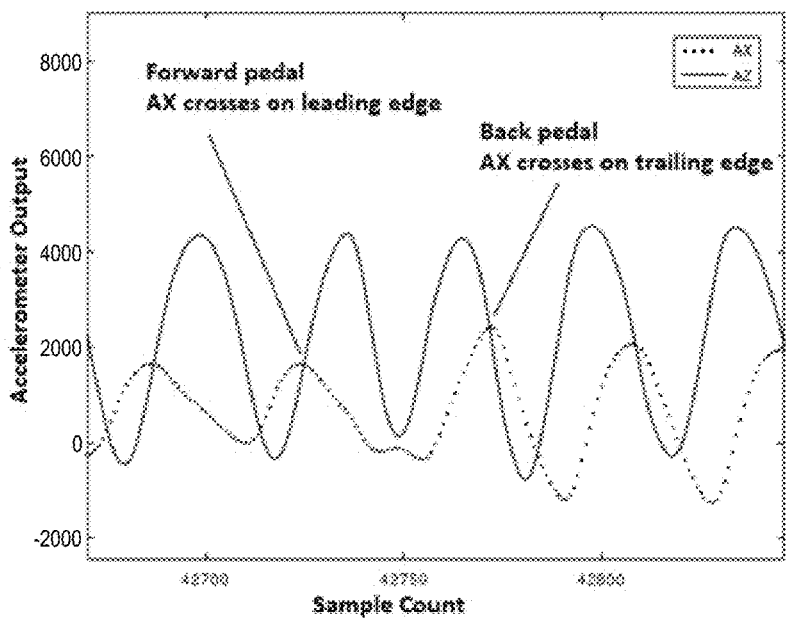
FIG. 15 is a graph 1501 showing motion sensor phase changes between forward and backward pedal strokes, according to some embodiments of the present invention.

FIG. 15 shows the intersection of two motion sensors at orthogonal orientations. Pedaling in the forward directions results in signal crossings at different phase positions than pedaling in the backward direction. During one pedal cycle there is one peak of each AZ and AX sensor. In some embodiments the peaks around sample count 42,700 show AZ peaks with a higher sample count than AX (forward pedaling). At around sample count 42,800 the AZ peaks with a lower sample count than AX (back pedaling). Simple subtraction of peak sample counts will be either a positive or negative difference, signaling forward or backward pedaling. (Note that only valid pedaling involves backpedal detection. If the rider is only flexing the foot, the accelerometer amplitudes will not rise to the level indicating a valid pedal stroke.)

In some embodiments, Back-Pedal detection is configured to control one or more of many different features, such as changing information screens on handle-bar mounted displays, changing songs being played across a wireless ear bud, marking beginning-end points of a hill which you want to time-analyze post ride, send notice to other riders in your group, etc.

Figure 10A:
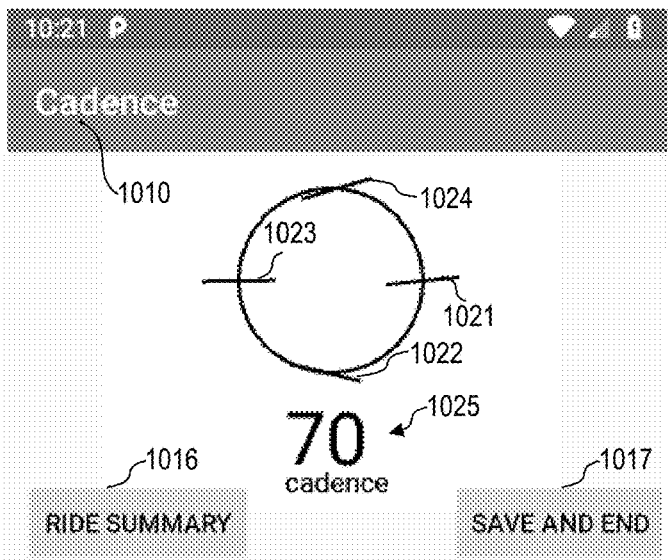
FIG. 10A is a screen shot from a Run-Time display 1001 of cadence and Pedal Angles, according to some embodiments of the present invention.

FIG. 10A is a screen shot from a Run-Time display 1001 of cadence and Pedal Angles, according to some embodiments of the present invention. In some embodiments, Run-Time display 1001 includes a screen identifier 1010 (in this case, indicating the "Cadence" screen, a first action button 1016 (in this case, receiving input of a user pressing the "Ride Summary" button to change the display from a continuous updating of the display with the four angles of the most recent stride as shown in this example, to a summary screen of an entire ride, for example), a second action button 1017 (in this case, receiving input of a user pressing the "Save and End" button to save all data and end the program, for example), a numerical output 1025 of the present stride rate, and four angle indications 1021, 1022, 1023 and 1024 of the four measured angles of the most recent stride, which in some embodiments, are continuously calculated and updated on the display.

This continuously updated foot-angle information display provides very useful feedback to the user for instantaneous physiological behavior modification and performance improvement.

Figure 10B:
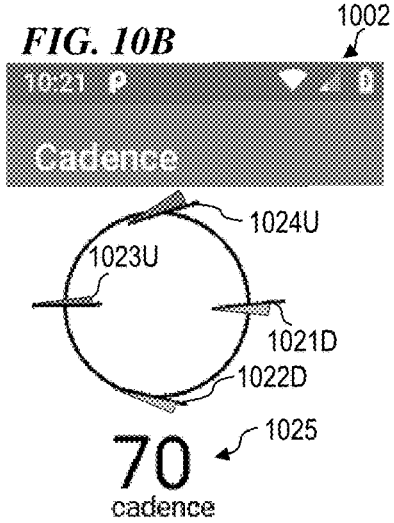
FIG. 10B is a screen shot from another Run-Time display 1002 of cadence and Pedal-Angle comparisons, according to some embodiments of the present invention.

FIG. 10B is a screen shot from another Run-Time display 1002 of cadence and Pedal-Angle comparisons, according to some embodiments of the present invention. In some embodiments, Run-Time display 1002 is substantially similar to Run-Time display 1001, but with the addition of small arcs shown along with each of the four foot-angle indicators, wherein the arcs graphically represent the amount and direction of angular difference between the user's foot angles and some predetermined "ideal" foot angle at each of the plurality of o'clock positions. In the example shown, angles and arcs 1023U and 1024U indicate that the "ideal" foot angle is up relative to the user's measured foot angle at the 9-o'clock and 12-o'clock positions, respectively, and angles and arcs 1021D and 1022D indicate that the "ideal" foot angle is down relative to the user's measured foot angle at the 3-o'clock and 6-o'clock positions respectively.

The run-time display be programmed to show the pedal angles with simple black lines (shown below) or the user could activate a color control to change the angle lines to the color red if the pedal angle is out-of-range. Run-Time Analysis of cadence and pedal angles offers a unique opportunity to understand pedal position and angle during rotation. Opinions vary on the optimal pedal positions and this invention provides an opportunity to more cost/effectively provide data to improve the conversations around the subject. Early indications are that pedaling profiles vary significantly and are difficult to change, much like a person's personality. This invention could yield a set of unique profiles for groups of riders that can be shared and compared on social media. In addition to using this invention to help train users to a specific pedaling style, simple modifications to existing pedaling habits can be programmed to encourage smaller changes for performance or comfort improvements.

Figure 16:
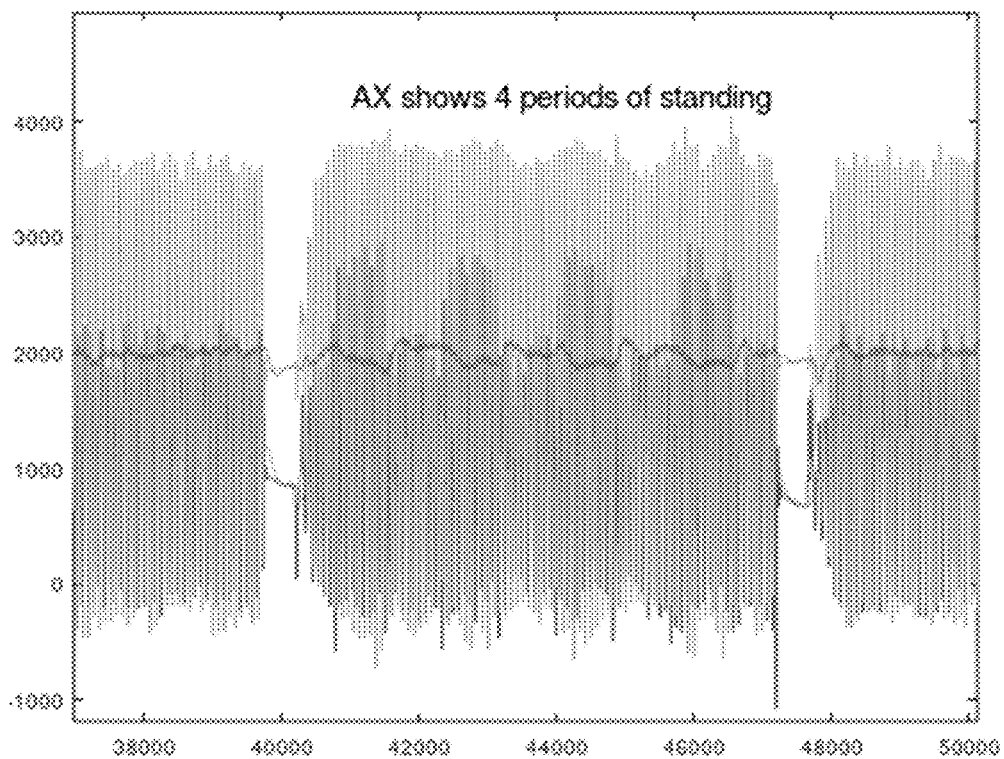
FIG. 16 is a graph 1601 showing motion sensor magnitude changes when a rider pedals in a standing position, according to some embodiments of the present invention.

FIG. 16 shows one of several methods of determining change in rider position. In this case the change in pedal forward angle (AX) shows the rider is pedaling in a standing position. The rider stands four consecutive times, executing ten (10) pedal strokes on each stand.

Cycle Wheel Monitoring

Speed—In some embodiments, the bicycle speed is determined by timing each revolution of the wheel, and using the wheel circumference and the timing to calculate speed.

Figure 11:
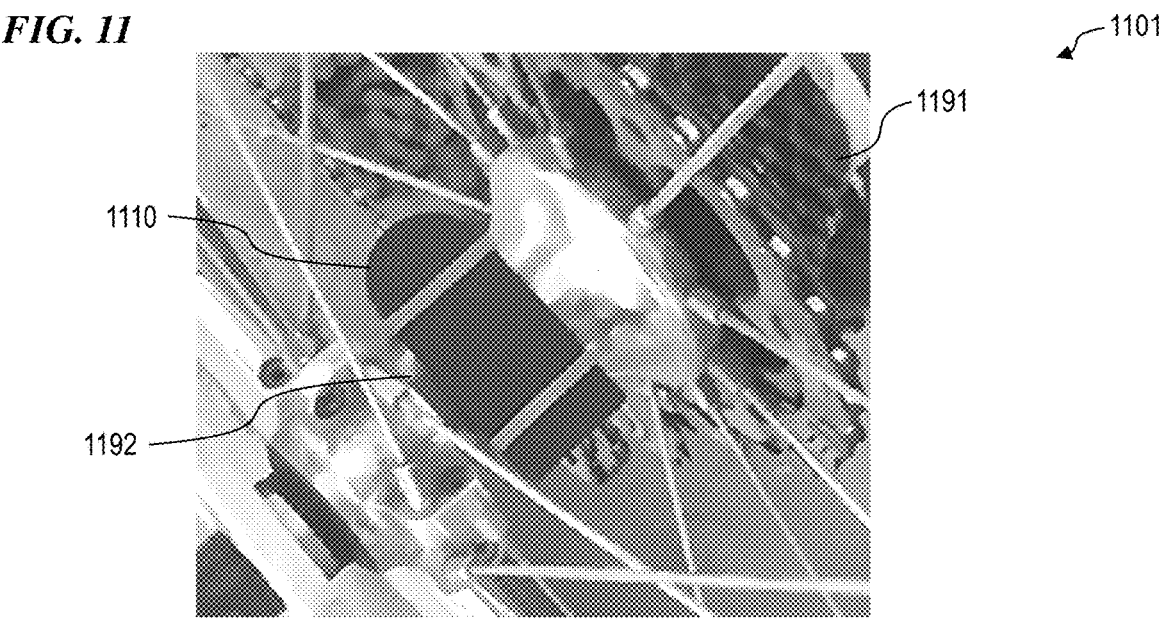
FIG. 11 is a perspective diagram 1101 from a photograph of a sensor mounted on a bicycle axle, according to some embodiments of the present invention.

FIG. 11 is a perspective diagram 1101 from a photograph of a sensor mounted on a bicycle-wheel axle, according to some embodiments of the present invention.

$$Pi*27 \text{ inches(wheel diameter)} = 84.8\text{-inch circumference}$$

$$5{,}280 \text{ feet}*12 \text{ inches} = 63{,}360 \text{ inches}$$

$$RPM = 60/(\text{rotation milliseconds})$$

$$(84.8*RPM*60)/63{,}360 = MPH$$

Power (w/trainer)—Stationary resistance trainers are calibrated to apply specific resistance at varying speeds. The formula is provided by the device manufacturer.

$$power(i) = (5.2448*speed(i)) + (0.019168*speed(i)^3);$$
$$endfor;$$

Figure 12:
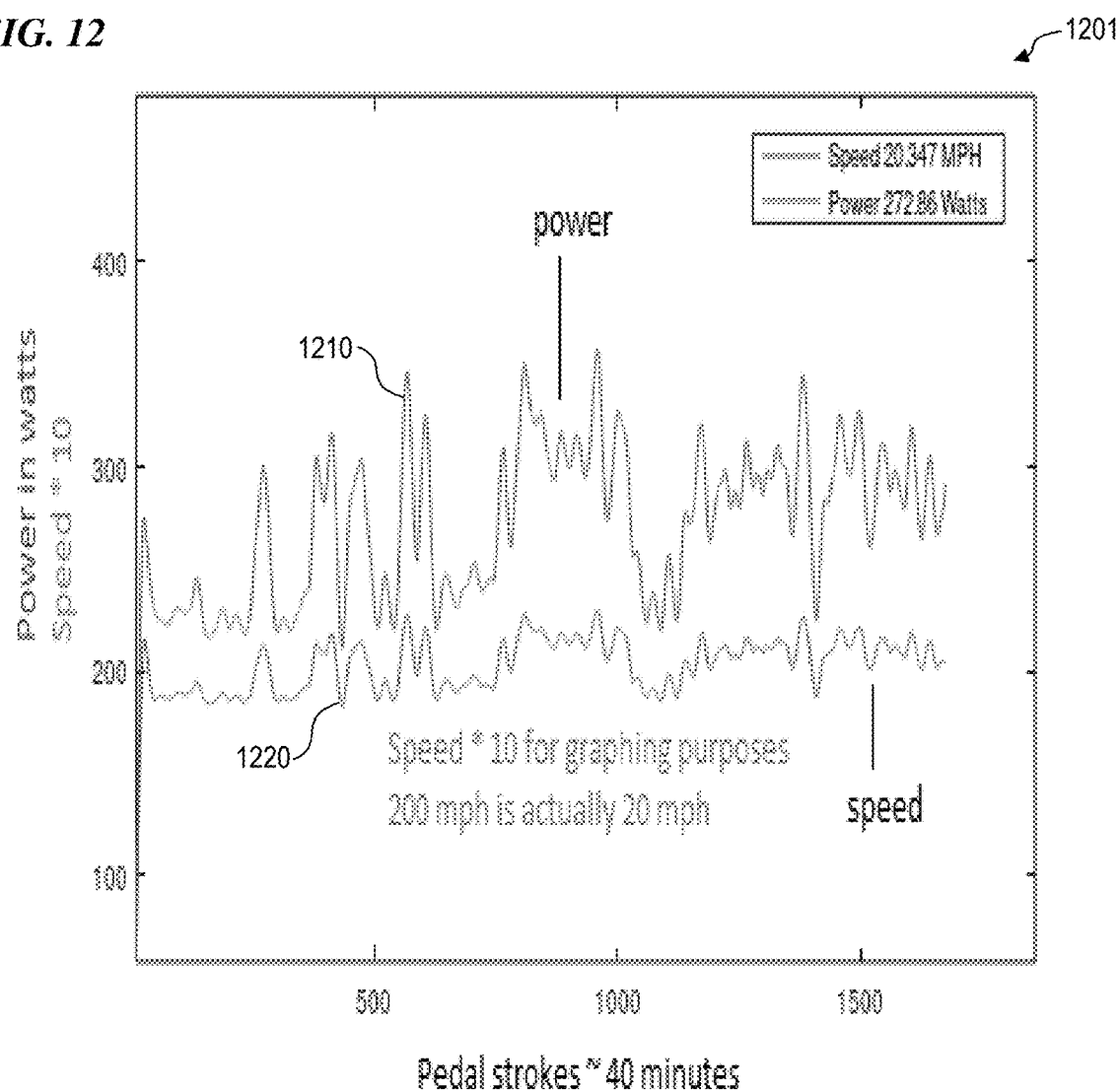
FIG. 12 is a graph 1201 of power versus time from a 40-minute bicycle ride, based on Sensor-calculated Speed/Power, according to some embodiments of the present invention.

FIG. 12 is a graph 1201 of power versus time from a 40-minute bicycle ride, based on Sensor-calculated Speed/Power, according to some embodiments of the present invention.

Wheel and Cadence Combined—With one sensor on the wheel and one on a shoe, shifting gears can be tracked. Shifting frequency and timing with cadence (too early/late) can be analyzed.

Pedaling Score

In some embodiments, a pedaling score is based on one or more (weighted) metrics: cadence, pedal angles, pedal angle range, foot tilt, foot rotation, waveform stability, and possibly gear shift-timing. In the sport of cycling, riders typically compete against time, speed and power. With the pedal score provided by this invention, riders can now compete against measures of technique. A pedal monitoring will allow riders to compete against themselves and others. In some embodiments, the game is in the form of an imaginary course of varying speeds, measuring the rider's ability to maintain proper pedaling technique. In some embodiments, the final score is weighted based on the rider's experience, allowing beginners and professionals to each compete on a more even playing field.

Mechanical-Fault Detection

In some embodiments, data abnormalities are used to identify equipment mechanical problems. During development, a foot-mounted sensor showed regular signal spikes only when monitoring the user's left foot on a specific bicycle. The issue remained unresolved until three (3) months later when the rider noticed a crack on the left pedal-crank arm. Thus, in some embodiments, the software of the present invention is calibrated to detect and notify the user of certain mechanical defects and/or bicycle maladjustments.

In some embodiments, the signals from the present system are used to generate and output specific adjustments to the bicycle (such as seat-post height, the forward-backward adjustment to the seat and/or handlebars, or the height of the handlebar post that can be made by the user or by a professional bicycle-fitting company to better fit the bicycle to the anatomy and/or pedaling style to the user in order to make it easier for the user to improve their pedaling form.

Run Monitoring

The sensor device described in this invention is similar in many ways to foot sensors that measure running activity. Combining the latest data analytics technology with preformatted and filtered running-stride input from this sensor of the present invention creates an opportunity to provide run monitoring uniquely calibrated to individual athletes. In some embodiments, since all activity data is saved, that data can be sent to an analysis service that executes software of the present invention and/or analysis software that returns data for run-time programs and/or visual and/or audio output data that are used by the device to measure and present, in real-time during a run, an interpretation of the runner's form, speed and distance of the runner's workout.

In some embodiments, the process of the present invention's hardware and software starts with the runner creating a reference set of data. With one or more sensors mounted on the runner's shoe(s), the human runner moves (runs) for a few minutes at ever-increasing speed. For example, in some embodiments, the human user begins by first walking at 3 miles per hour (as measured by the sensor, or by a GPS device, or by a mechanical treadmill or the like) for a couple minutes, then jogging at 4 and then 5 miles an hour, finally running at 6 and 7 miles an hour.

In some embodiments, the present invention extracts a range of features from the data of the human runner's sensor(s), and then executes a correlation analysis to determine whether an accurate predictor equation is identified. In one case, the present invention simply used the forward motion accelerometer data, along with run cadence measured by the peak of the gyroscope pitch angle.

Figure 13:
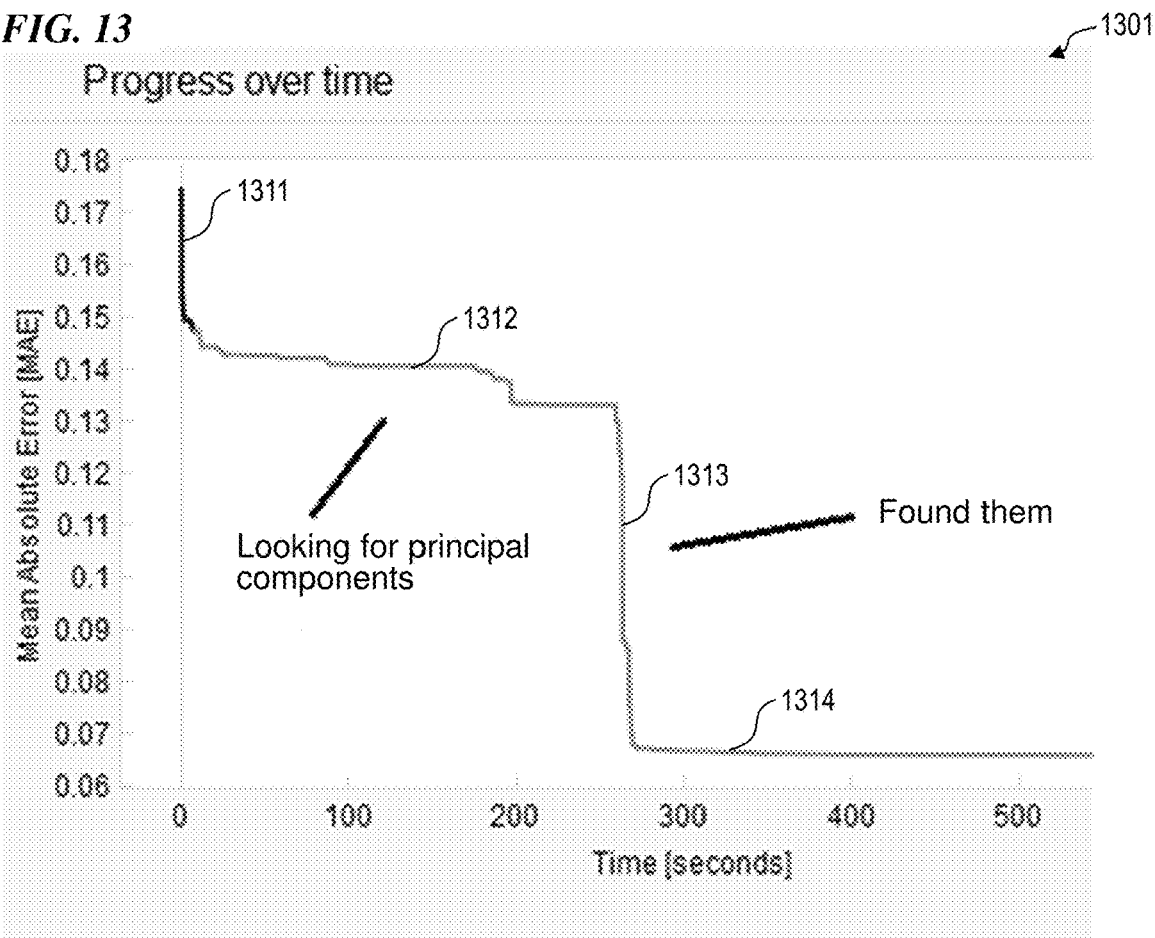
FIG. 13 is a graph 1301 showing progress (based on mean absolute error magnitude) during a processor calculation of Correlation Analytics Run Time and Error Rate, according to some embodiments of the present invention.

FIG. 13 is a graph 1301 showing calculation progress (based on the mean absolute error magnitude) during a processor calculation of Correlation Analytics Run Time and Error Rate for a person who was running using foot-angle sensors and processor analysis of the present invention, according to some embodiments of the present invention.

Figure 14:
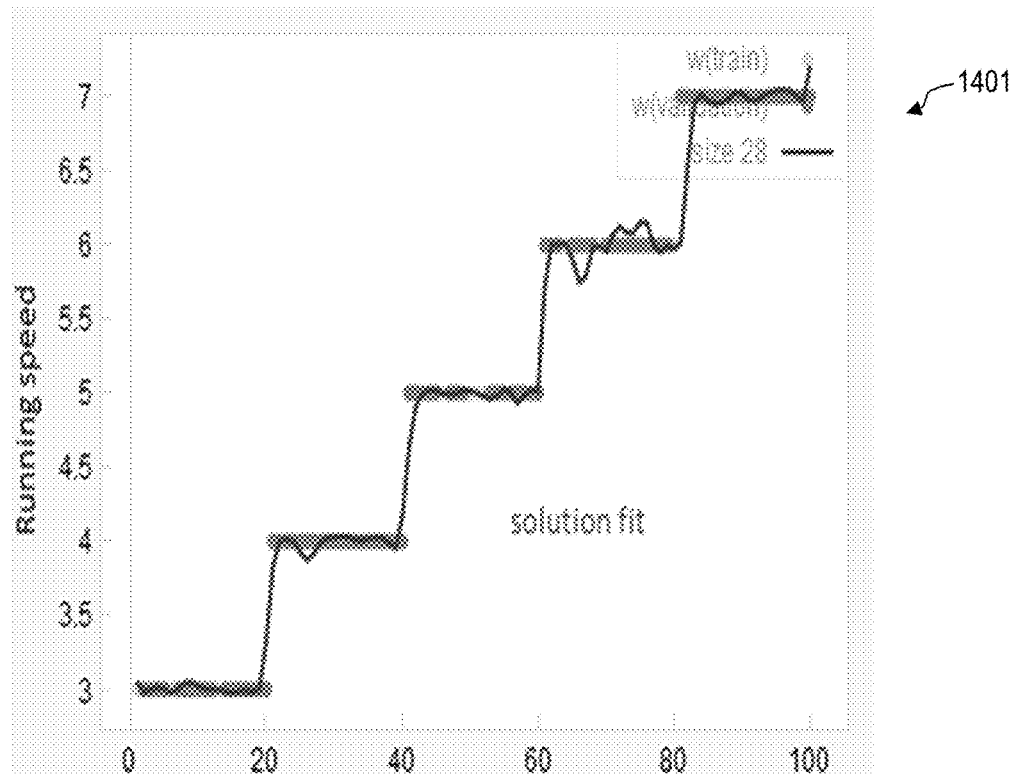
FIG. 14 is a graph 1401 of Running Speed and Solution Fit, according to some embodiments of the present invention.

FIG. 14 is a graph 1401 of Running Speed and Solution Fit, for a person who was running using foot-angle sensors and processor analysis of the present invention, according to some embodiments of the present invention.

The calculation shown in FIG. 14 uses calculations of AX total (x) (based on accelerometer data) and GX peak (y) (based on gyroscopic sensor data) for a person who was running using foot-angle sensors and processor analysis of the present invention, to determine speed (w)

$$\text{Speed} = 1.31 + 2.14e{-}5{*}x + 9.73e{-}9{*}y^2 - 0.22{*}\sin(1.89 + 0.00014657{*}x + 5.90e{-}8{*}y^2)$$

$R^2$ Goodness of Fit: 0.98996783

In some embodiments, analyzing a wide range of runner data, with different shoes on unique terrain, provides a default run-time program as a product default. Unique run-time programs are an option for users wanting personalized running analysis.

Figure 17A:
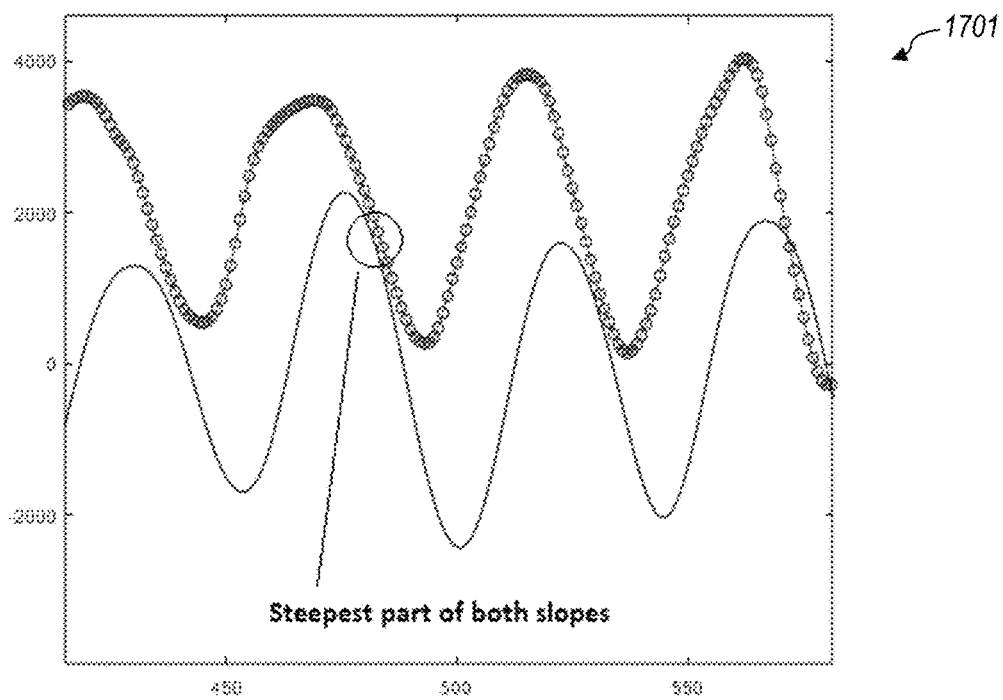
FIG. 17A is a graph 1701 that has plots of acceleration measurements and rotational measurements during four strides during a bicycle ride, according to some embodiments of the present invention.
Figure 17B:
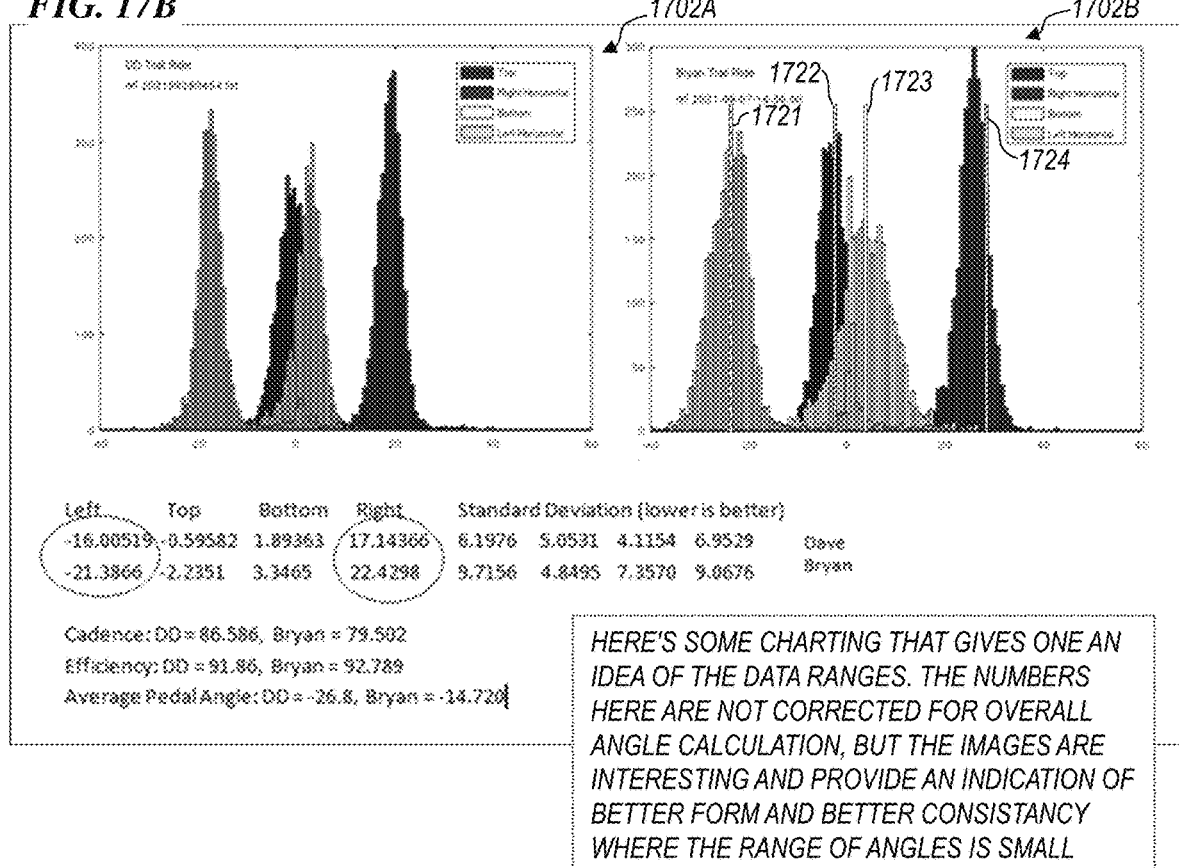
FIG. 17B includes histogram graphs of the foot-angle distributions 1702A of a first bicycle-rider's foot angles at four o'clock foot-angle-measurement positions (TDC at 12-o'clock, right-horizontal at 3-o'clock, BDC at 6-o'clock and left-horizontal at the 9-o'clock position), and the foot-angle distributions 1702B of a second bicycle-rider's angles at the four o'clock foot-angle-measurement positions, according to some embodiments of the present invention.
Figure 17C:
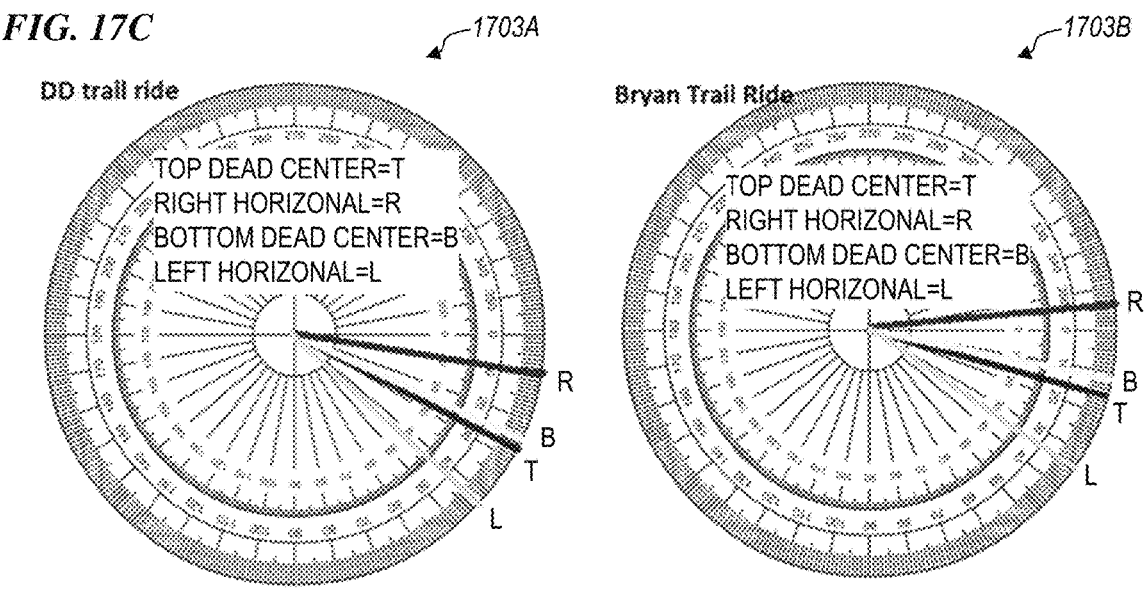
FIG. 17C are graphical representations that include angle representations of the foot-angle measurements 1703A of a first bicycle-rider's foot angles at the four o'clock foot-angle-measurement positions (12-, 3-, 6-, and 9-o'clock positions), and the foot-angle measurements 1703B of a second bicycle-rider's angles at the four o'clock foot-angle-measurement positions, according to some embodiments of the present invention.

FIG. 17A is a graph 1701 that has plots of acceleration measurements and rotational measurements during four strides during a bicycle ride, according to some embodiments of the present invention.

FIG. 17B includes histogram graphs of the foot-angle distributions 1702A of a first bicycle-rider's foot angles at four o'clock foot-angle-measurement positions (TDC at 12-o'clock, right-horizontal at 3-o'clock, BDC at 6-o'clock and left-horizontal at the 9-o'clock position), and the foot-angle distributions 1702B of a second bicycle-rider's angles at the four o'clock foot-angle-measurement positions, according to some embodiments of the present invention. In some embodiments, the desired or ideal angles 1721, 1722, 1723 and 1724 are also displayed overlaid on the same four histograms, and in some embodiments (not shown) an instantaneous indication of the angles of the most recent stride are displayed and highlighted as they accumulate on the four histograms.

FIG. 17C includes angle representations of the foot-angle measurements 1703A of a first bicycle-rider's foot angles at the four o'clock foot-angle-measurement positions (12-, 3-, 6-, and 9-o'clock positions), and the foot-angle measurements 1703B of a second bicycle-rider's angles at the four o'clock foot-angle-measurement positions, according to some embodiments of the present invention.

Figure 18A:
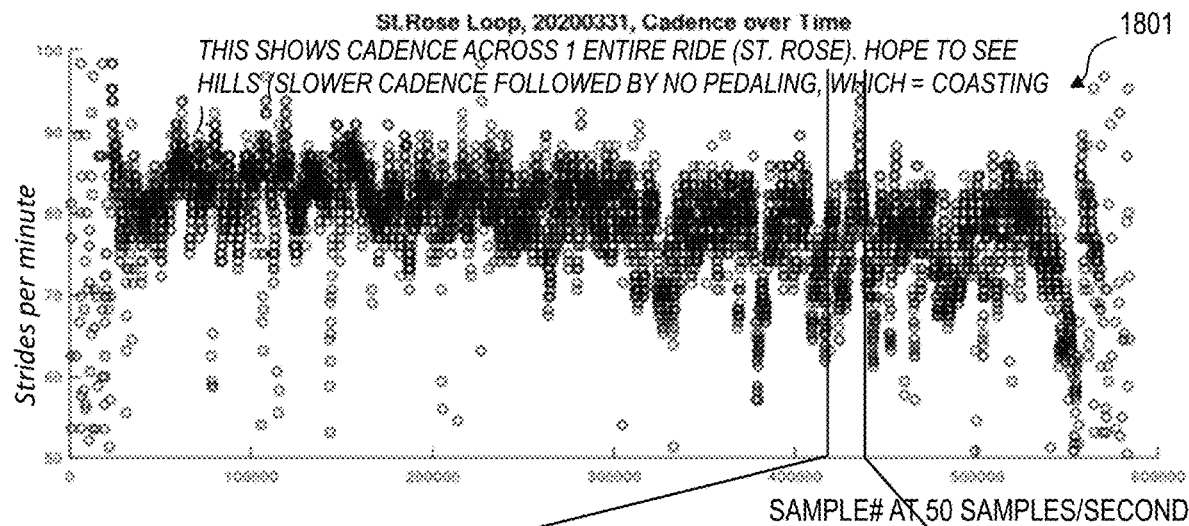
FIG. 18A is a graph 1801 of over 500,000 stride-rate measurements (labeled 0 to 600,000 along the X axis, wherein the stride rates are between 50 and 100 strides per minute along the Y axis) during a bicycle ride along a route labeled "St. Rose Loop", according to some embodiments of the present invention.

FIG. 18A is a graph 1801 of over 500,000 stride-rate measurements (labeled 0 to 600,000 along the X axis, wherein the stride rates are between 50 and 100 strides per minute along the Y axis) during a bicycle ride along a route labeled "St. Rose Loop", according to some embodiments of the present invention.

Figure 18B:
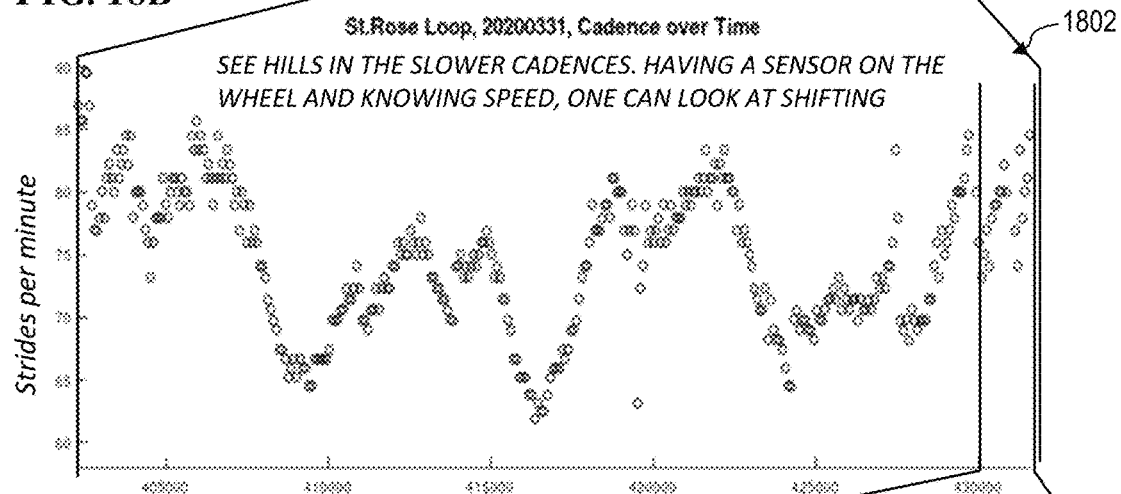
FIG. 18B is an enlarged graph 1802 of a portion of the stride-rate measurements (those labeled between about 402,000 and 435,000 along the X axis, wherein the stride rates are between 60 and 90 strides per minute along the Y axis) during a portion of the bicycle ride along route "St. Rose Loop", according to some embodiments of the present invention.

FIG. 18B is an enlarged graph 1802 of a portion of the stride-rate measurements (those labeled between about 402,000 and 435,000 along the X axis, wherein the stride rates are between 60 and 90 strides per minute along the Y axis) during a portion of the bicycle ride along route "St. Rose Loop", according to some embodiments of the present invention.

Figure 18C:
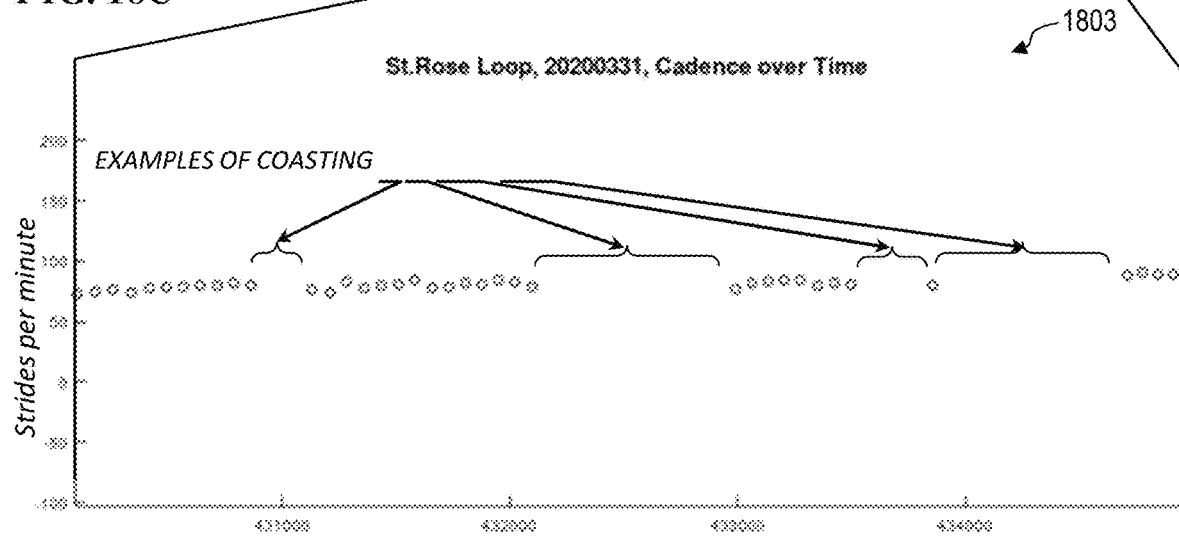
FIG. 18C is a further-enlarged graph 1803 of a portion of the stride-rate measurements (those labeled between about 430,000 and 435,000 along the X axis, wherein the stride rates are between about 70 and 80 strides per minute along the Y axis, but show gaps in the successive dots (small circles) where the user is coasting (not performing full circular strides, even though the user may be moving the pedal back and forth during those coasting periods) during a portion of the bicycle ride along route "St. Rose Loop", according to some embodiments of the present invention.

FIG. 18C is a further-enlarged graph 1803 of a portion of the stride-rate measurements (those labeled between about 430,000 and 435,000 along the X axis, wherein the stride rates are between about 70 and 80 strides per minute along the Y axis, but show gaps in the successive dots (small circles) where the user is coasting (not performing full circular strides, even though the user may be moving the pedal back and forth during those coasting periods) during a portion of the bicycle ride along route "St. Rose Loop", according to some embodiments of the present invention.

In some embodiments, the display output includes adjustable color parameters for the system's suggestions for improving the user's athletic form, such as gentle changes to the color's intensity, hue and saturation, that provide constructive behavior-modification hints (e.g., slower and/or more subtle color changes as the user changes their foot angles towards or away from the "ideal" angles, as opposed to sudden and/or stark color changes that tend to have a maladaptive behavior responses from some bicycle riders), wherein the colors used to render angled lines, bar graphs, or color text that the system of the present invention outputs and that are for the user to use for changing different parts of their bicycling or running stride. In some embodiments, the parts of the bicyclist's stride include foot angle and rate of toe extension and retraction, whether the rider is "pedaling while standing" (striding while not seated on the bike's saddle), and if so, then whether the rider is too far forward or too far back, rather than keeping their weight directly over the pedals, and whether the rider is maintaining at least a slight bend at the knee when standing even at the bottom of the pedal stroke. In some embodiments, the present invention tracks the proportion of a ride is done standing up out of the saddle, since too much riding while on the seat may put too much stress on the knees for some people, but may improve aerodynamic efficiency.

In some embodiments, the display output includes a colored histogram (e.g., representations of one or more three-dimensional surfaces shown as perspective views of a multi-dimensional histogram) that indicate improvements that could be made, e.g., by showing (see FIG. 17B) the local maxima (indicating the most-frequent angle) and the width (indicating variance in angles) of each of the user's left-foot and right-foot angles at each of the four "o'clock positions" (see FIG. 8A). In some embodiments, the graphical representations provide simultaneous indications from a larger set of variables, such as additionally showing cadence consistency over different portions of a ride, frequency and appropriateness of timing of gear shifting (which can help keep a consistent cadence), how much the bicycle tilts left-to-right while pedaling standing up ("wonking"), the sensed weaving of the path ridden, and the like.

In some embodiments, the display output includes graphical guidance as to how to better change the user's rates of muscle extension and contraction between noon-3-6-9 o'clock positions, so to reach the desired angles at those four points of each stroke for each foot.

In some embodiments, the present invention includes audio-output feedback, based on the system's interpretation of the user's efficiency or form, and adjusts the rate/beat/syncopation or loudness or frequency of the user's song track or other audio that is listened to while competing or working out.

In some embodiments, the present invention includes haptic-output buzzers (which are adjusted so as not to be misinterpreted by the user to be "buggers"), tappers, or clickers in a wrist strap or angle strap or headband that are configured to buzz or click at a particular o'clock of the stroke to signal to the user when to initiate an extension or to inhibit bad form habits. In some such embodiments, this provides cadence feedback to help manage variations is stride rate.

In some embodiments, the present invention includes electrical signal-output electrodes, that provide very slight electrical nerve-stimulation shocks or transcutaneous electrical "ticks" or "buzzing" from electrodes in a wrist strap or angle strap or headband that are configured to buzz or click to the user's muscles at a particular o'clock of the stroke to signal to the user when to initiate an extension or to inhibit bad form habits. In some such embodiments, this provides cadence reinforcement or non-reinforcement (also called "feedback") to help manage variations is stride rate.

In some embodiments, the present invention includes electrical signal-input electrodes, that provide signal inputs to the processor for muscle-function and/or nerve-function sensing and/or heart monitoring. These input electrodes and signal sensors and amplifiers are optional additional sensors for electromyogram (EMG) electrical sensing on leg muscles, or electrocardiogram (ECG) heart straps.

In some embodiments, the present invention includes chest straps that have tension sensors or the like, that provide signal inputs to the processor for breath-rate monitoring. In some embodiments, the processor uses GPS location sensors and stored or fetched terrain maps to determine when and where an upcoming uphill portion of the ride is approaching and to indicate to the bicyclist to increase their breath rate to pre-oxygenate their blood for the anticipated additional exertion of hill climbing.

In some embodiments, the present invention includes ECG-monitor-sensor outputs integrated into the game display so the user can help themselves avoid heart stress or a heart attack during a bike ride.

In some embodiments, the present invention includes graphical and/or numerical output that guide the post-height and seat-forward/back adjustments of a bicycle so as to improve the various foot angles so to provide bike fitters with additional services that they can configure and customize based on their other expertise.

In some embodiments, the present invention includes further display output that includes time-varying form score(s) for the most recent ten pedal strokes (moving average and variance), as well as score(s) for most recent five minutes (average(s) and variance for each form) and for today's entire ride and cumulative weekly, monthly or yearly form scores for the user and the user's selected group of persons with whom to compete. "Good" riders may be deemed to have high scores and low variance. For some human users, perhaps consistency at a given form is better than changing form to chase some other accuracy or perfection of form.

In some embodiments, the present invention includes a game implementation for bicyclists that includes measuring and gathering multi-variable scores that are compared to scores of top riders or riders of the same or different body sizes and types.

In some embodiments, the present invention provides an apparatus, method and/or non-transitory computer-readable medium for use by professional bike fitters to help them adjust distances and angles between and among the seat, handlebar, and pedals, the length of the crank to the pedals and other variable parameters of a custom-built bicycle, in order that the bicycle is more efficient and comfortable for a particular bicyclist.

In some embodiments, the present invention measures pedal angles relative to the ground at a plurality of angles as the pedal crank makes each rotation.

TABLE 1

Some example measurements of various user's foot angle to ground

| Foot Angle to ground desired range | 12 o'clock 20 to low 30's | 3 o'clock 10 to 12 | 6 o'clock 5 to 20 | 9 o'clock 40+ |
|---|---|---|---|---|
| DaveL May 27, 2022 | 23 | *9* | *32* | 44 |
| DaveD May 31, 2022 | 26 | 11.6 | *33.5* | 46.1 |
| DaveL May 31, 2022 | 23 | *3.4* | *33.5* | 47.9 |
| Bryan May 31, 2022 | 23 | *-3.5* | *24* | 49 |
| Geoff Jun. 8, 2022 | 26 | *12* | *39* | 50 |

(The bold-italic-underlined values are outside the preferred or desirable range.)

TABLE 2

Foot Angle Range (Q1-12 to 3 o'clock) (Smaller Number Is Better)

| Foot Angle (12-3 o'clock) | Left Foot | Right Foot | Level |
|---|---|---|---|
| DaveD (May 31, 2022) | | 15 | Exceptional |
| DaveL (May 27, 2022) (May 31, 2022) | 19.3 | 13.4 | Exceptional |
| Bryan (May 31, 2022) | *21* | *27* | Moderate |
| Geoff Jun. 8, 2022 | | 14 | Exceptional |

(The bold-italic-underlined values are outside the preferred or desirable range.)

TABLE 3

Total Foot Angle Range (Smaller Number Is Better)

| Foot Angle Range | Left Foot | Right Foot | Level |
|---|---|---|---|
| DaveD (May 31, 2022) | | 35 | Exceptional |
| DaveL (May 27, 2022) (May 31, 2022) | 45 | 35 | Moderate/Exceptional |
| Bryan (May 31, 2022) | 39 | *52.2* | *Imbalance* |
| Geoff Jun. 8, 2022 | | 38 | Exceptional |

(The bold-italic-underlined values are outside the preferred or desirable range.)

Figure 19A:
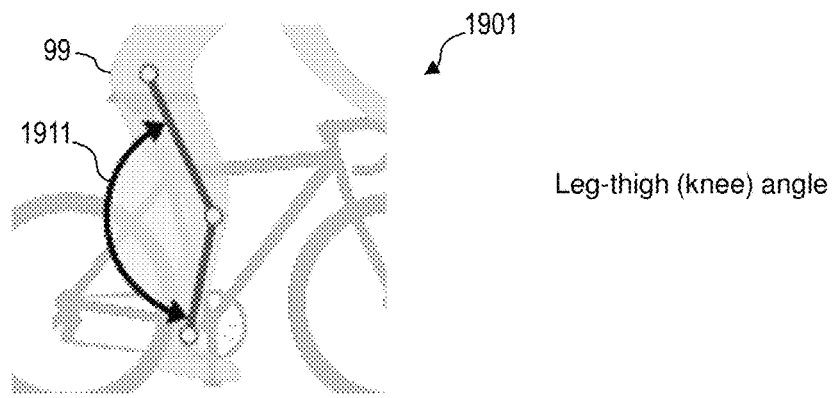
FIG. 19A is a side view 1901 of a bicyclist 99 illustrating the knee angle 1911 of the bicyclist's knee, also called (herein) the leg-thigh angle, according to some embodiments of the present invention.

FIG. 19A is a side view 1901 of a bicyclist 99 illustrating the knee angle 1911 of the bicyclist's knee, also called (herein) the leg-thigh angle, according to some embodiments of the present invention.

Figure 19B:
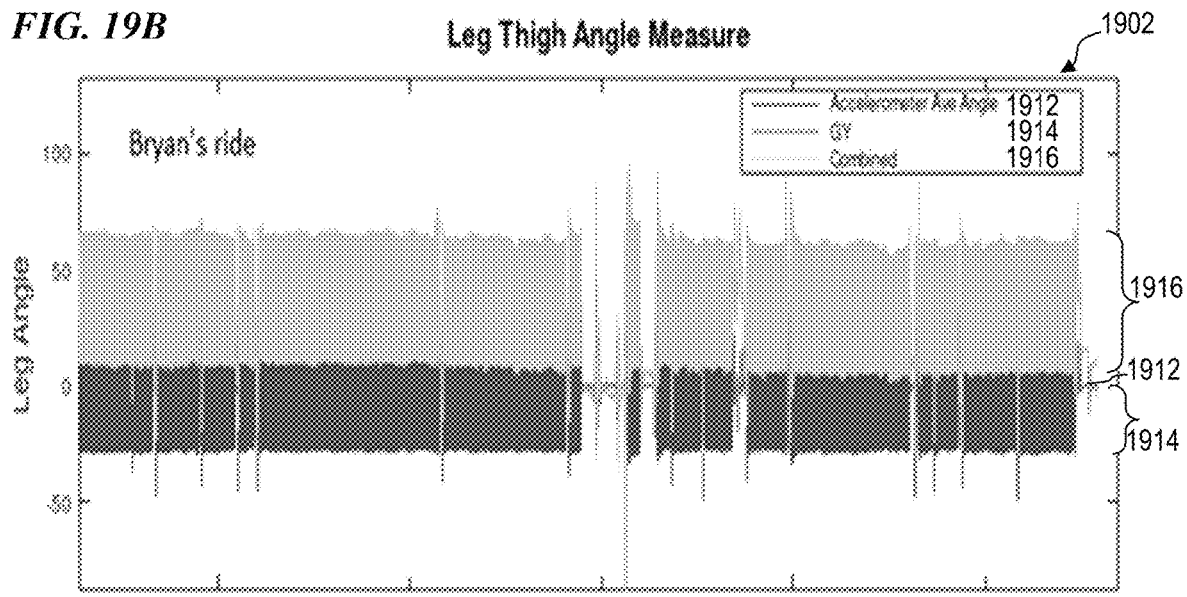
FIG. 19B is a graph 1902 of a first user's knee-angle measurements versus time, according to some embodiments of the present invention.

FIG. 19B is a graph 1902 of a first user's knee-angle measurements versus time, according to some embodiments of the present invention. In this graph 1902, the accelerometer average angle 1912 is mostly hidden behind the gyroscope measurements 1914 and the combined accelerometer and gyroscope measurements 1916. Here, there is relatively little variation in this user's measured knee angle (as represented by combined accelerometer and gyroscope measurements 1916) over the time period of the measurements.

Figure 19C:
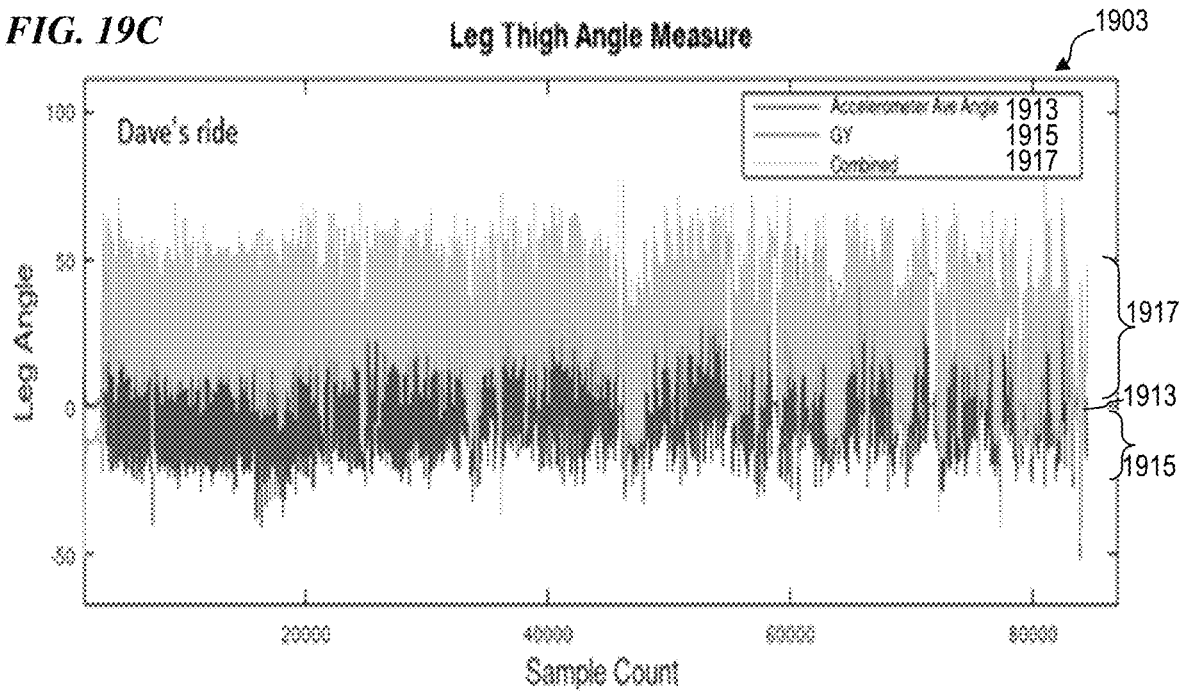
FIG. 19C is a graph 1903 of a second user's knee-angle measurements versus time, according to some embodiments of the present invention.

FIG. 19C is a graph 1903 of a second user's knee-angle measurements versus time, according to some embodiments of the present invention. In this graph 1903, the accelerometer average angle 1913 is mostly hidden behind the gyroscope measurements 1915 and the combined accelerometer and gyroscope measurements 1917. Here, there is relatively more variation in this second user's measured knee angle (as represented by combined accelerometer and gyroscope measurements 1917) over the time period of the measurements, as compared to FIG. 19B.

Figure 20A:
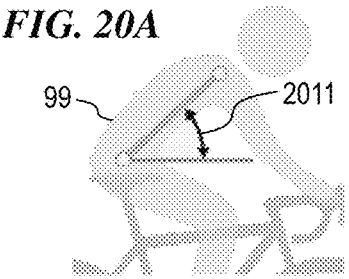
FIG. 20A is a side view 2001 of a bicyclist 99 illustrating the torso angle 2011 of the bicyclist's torso to the ground in a forward-backward direction, according to some embodiments of the present invention.

FIG. 20A is a side view 2001 of a bicyclist 99 illustrating the torso angle 2011 of the bicyclist's torso to the ground in a forward-backward direction, according to some embodiments of the present invention.

Figure 20B:
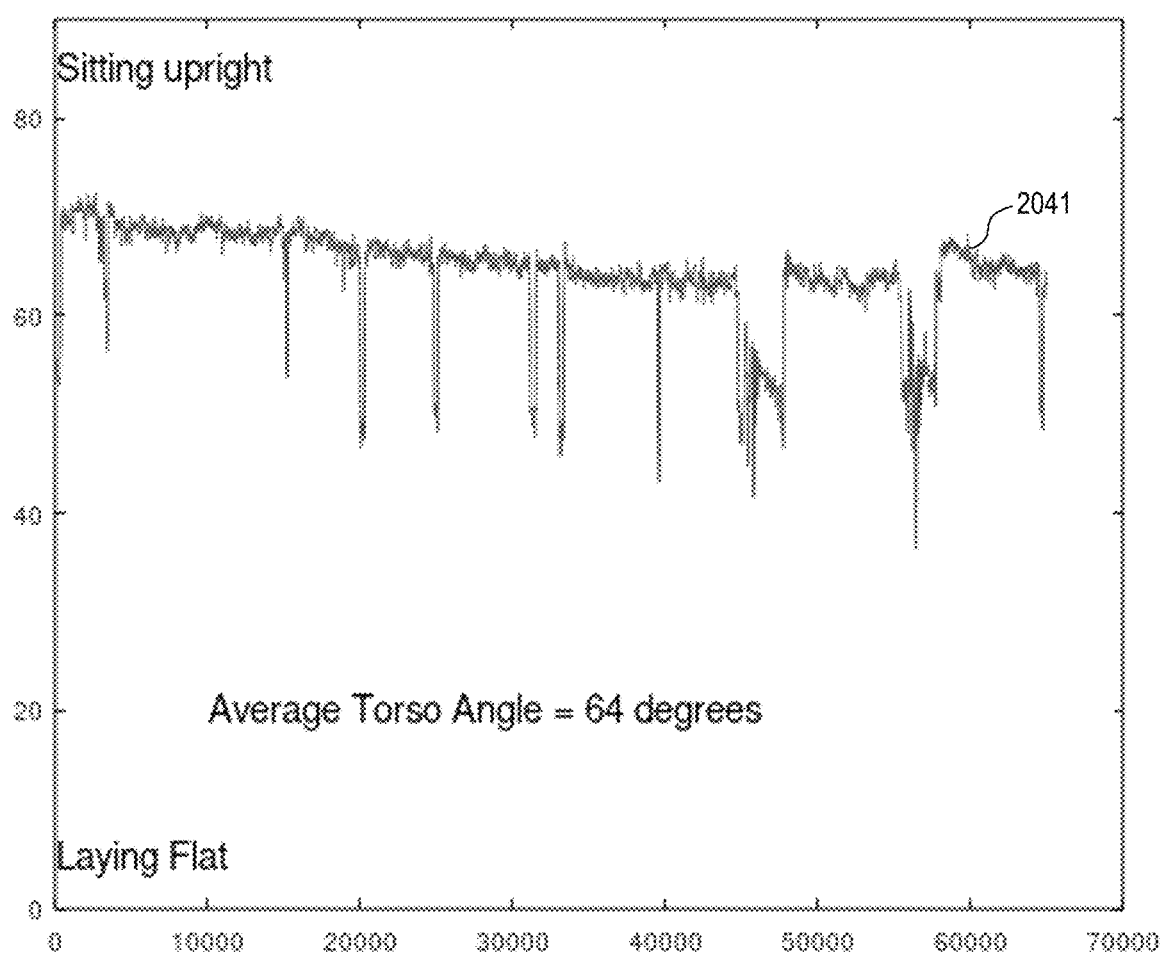
FIG. 20B is a graph 2002 of a third user's torso-angle measurements 2041 versus time, according to some embodiments of the present invention.

FIG. 20B is a graph 2002 of a third user's torso-angle measurements 2041 versus time, according to some embodiments of the present invention. This graph 2002 of the torso angle 2011 (see FIG. 20A) shows that over the time period of the ride (about twenty minutes of evenly spaced samples), the average torso angle was 64 degrees, but the additional information of this graphical presentation provides the additional information that the torso angle was steadily going down over the course of the twenty-minute uphill ride with occasional spikes downward (leaning further down by resting elbows on handlebars when stopped for a minute), perhaps due to the rider being increasingly tired or other reasons (such as the angle of the hill changing) that the rider could become cognizant of having seen the graphical data by the present invention.

Figure 20C:
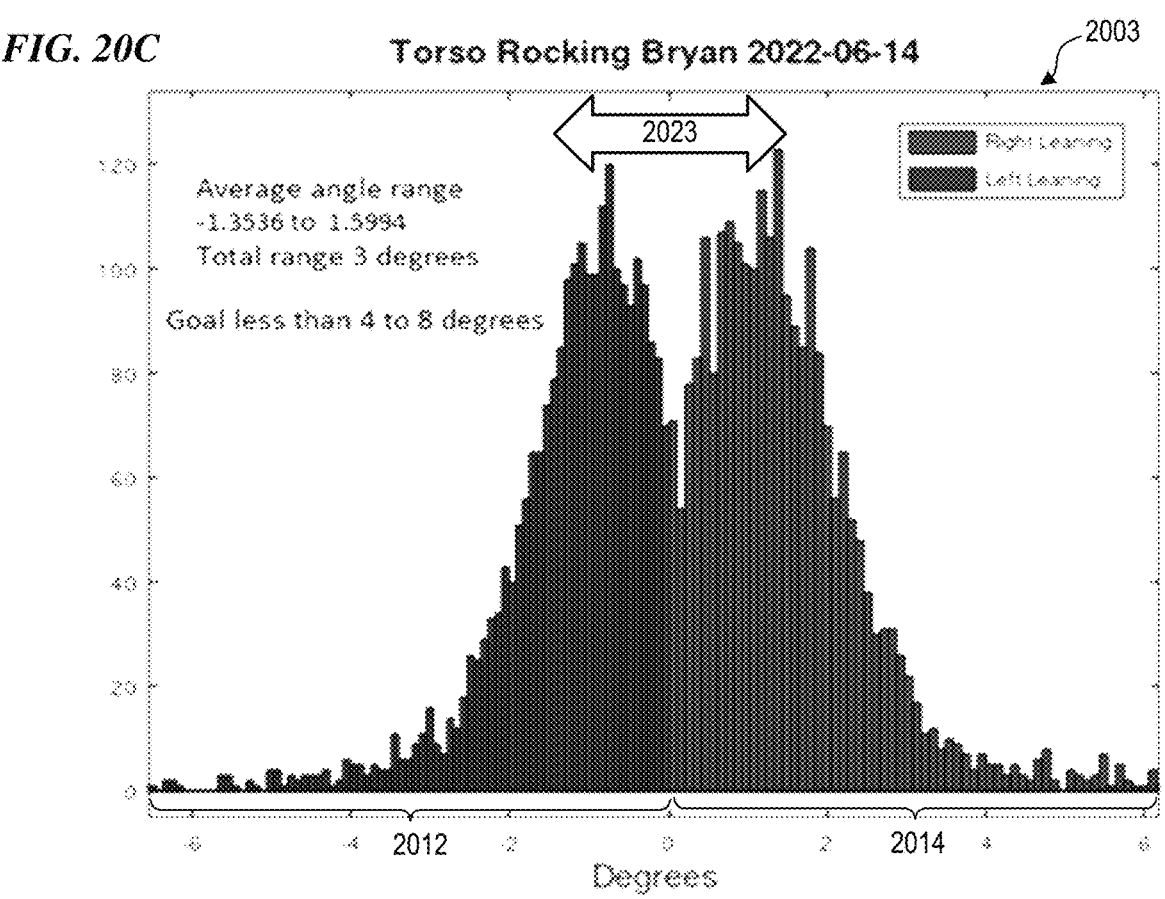
FIG. 20C is a histogram 2003 of a first user's torso-rocking-angle measurements, according to some embodiments of the present invention.

FIG. 20C is a histogram 2003 of a first user's torso-rocking-angle measurements, according to some embodiments of the present invention. The left-hand histogram portion 2012 are the right-leaning rocking (side-to-side) angles and the right-hand histogram portion 2014 are the left-leaning rocking angles. Here, the total range of angles 2022 is about 3 degrees, which is within a preferred or desired range of less than 4 to 8 degrees.

Figure 20D:
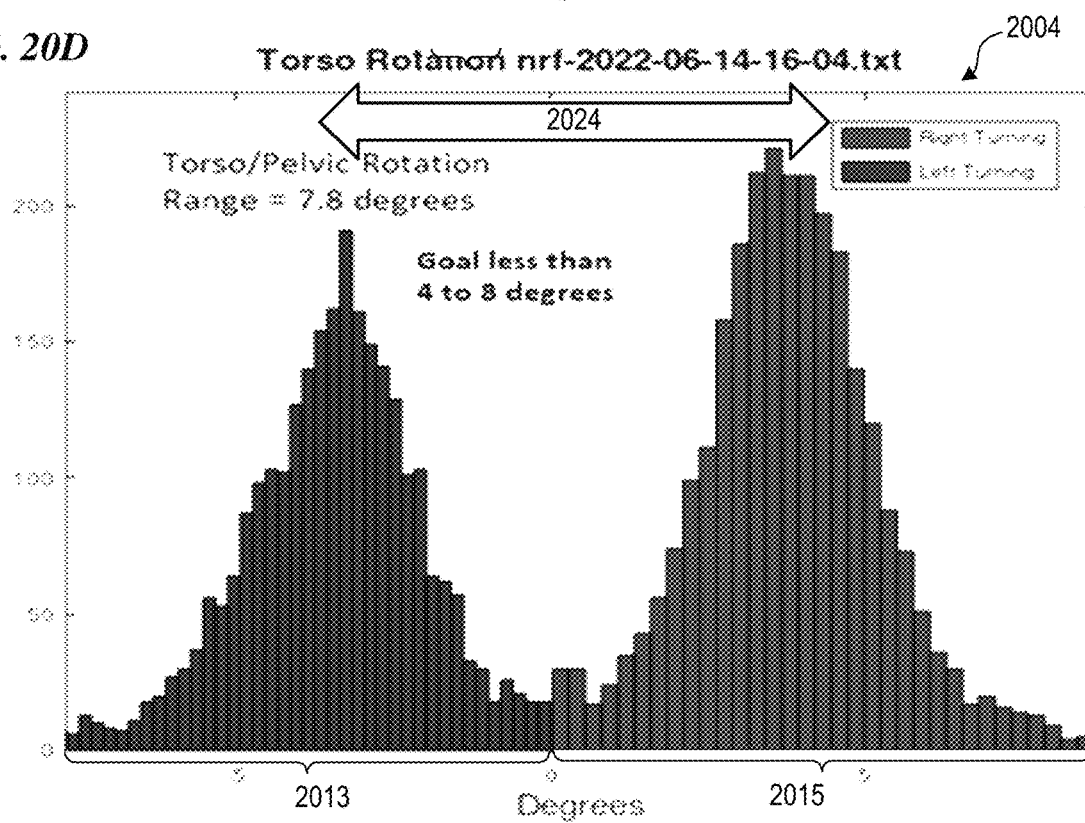
FIG. 20D is a histogram 2004 of a second user's torso-rocking-angle measurements, according to some embodiments of the present invention.

FIG. 20D is a histogram 2004 of a second user's torso-rocking-angle measurements, according to some embodiments of the present invention. The left-hand histogram portion 2013 are the right-leaning rocking (side-to-side) angles and the right-hand histogram portion 2015 are the left-leaning rocking angles. Here, the total range of angles is about 7.8 degrees, which is at the high end of the preferred or desired range of less than 4 to 8 degrees.

In some embodiments, the present invention provides IMU sensor measurements that are calibrated, phase-adjusted, and spline interpolated for use in robotics, and in particular, in a digital human (DH) robotic system that mimics human body motion.

Some embodiments further include measuring, recording and outputting the bicyclist's thigh-calf angle (e.g., the angle of the long axis of the femur to the long axis of the tibia, or the angle that the knee is bent at various o-clock positions of the pedal rotation such as top-dead-center (the 12-o-clock position of the pedal crank during each rotation), right horizontal (3-o-clock), bottom dead center (6-o-clock), and left horizontal (9-o-clock)). Some embodiments further include measuring, recording and outputting the bicyclist's torso angle relative to the ground, as well as pelvic and torso rocking and rotation using sensors mounted to the user's belt or shoulder.

In some embodiments, the present invention provides measuring and calibrating measurements as averaged over long rides. However, some embodiments also provide measurements that are averaged over short sequences in order to provide more finely specified data variations that can then be correlated to subsections of a bicycle ride and give more immediate feedback to the user.

Some embodiments include a temporal phase correction based on the differing response times of accelerometer sensors relative to gyroscopic sensors.

Some embodiments include a spline-interpolation algorithm that virtually increases apparent sample resolution without the system burden of increasing real sample rates.

Some embodiments further detect and compensate for the sensor position as it is moved between pedal-spindle position to various shoe locations outward towards the toe. (As an analogy, think of the fulcrum of a tetter-totter moving away from center and the effects on motion sensors at either extreme.)

In some embodiments, the present invention provides an apparatus that includes a portable personal electronic device, such as a cell phone, that wirelessly receives acceleration data and rotational data from a foot-mounted sensor module that includes at least two accelerometer sensors to provide acceleration measurements in at least two orthogonal directions and at least two gyroscope sensors to provide rotational or gyroscopic measurements around at least two orthogonal axial directions; a processor that calculates foot angles at a plurality of successive positions within each of a plurality of strides of a human user during an athletic activity; and an output device in the personal electronic device that presents human-perceptible indications based on the calculated foot-angle data.

In some embodiments, the output device includes a display that outputs graphical indications of calculated foot angle at a plurality of positions during each stride of a human user.

In some embodiments, the output device includes at least one audio output device that outputs audible indications of calculated foot angle at a plurality of positions during each stride of a human user.

In some embodiments, the athletic activity is cycling.

In some embodiments, the athletic activity is cycling, the plurality of successive positions within each of the plurality of strides of the human user correspond to at least three o'clock positions of a pedal crank of a bicycle, and the human-perceptible indications based on the calculated foot-angle are based on calculated foot angle at each one of the at least three o'clock positions of the pedal crank.

In some embodiments, the athletic activity is cycling, the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and the human-perceptible indications based on the calculated foot-angles are based on calculated foot angle at each one of the 12-o'clock position, the 3-o'clock position, the 6-o'clock position, and the 9-o'clock position of the pedal crank.

In some embodiments, the athletic activity is cycling, the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and the human-perceptible indications based on the calculated foot-angles are based on calculated foot angle at each one of the 12-o'clock position, the 3-o'clock position, the 6-o'clock position, and the 9-o'clock position of the pedal crank and on a comparison of the calculated foot angles of the user to a predetermined desired or "ideal" foot angle at each of the four o'clock positions.

In some embodiments, the athletic activity is cycling, the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, the human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions as compared to a closeness comparison of another user's calculated foot angle relative to the "ideal" foot angle at each of the four o'clock positions, and the output device presents a human perceptible indication of whether the user has a closer comparison to the "ideal" foot angles relative to the other user's comparison.

In some embodiments, the athletic activity is cycling, the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, the human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions at each of a plurality of geographical locations of a current bicycle ride along a first bicycle route as compared to a closeness comparison of the user's calculated foot angle relative to the "ideal" foot angle at each of the four o'clock positions at each of the plurality of geographical locations along the first bicycle route during a prior bicycle ride, and the output device presents a human perceptible indication at a plurality of geographical locations during the current bicycle ride of whether the user has a closer comparison to the "ideal" foot angles relative to the user's foot angles at the same locations during the prior bicycle ride.

In some embodiments, the athletic activity is cycling, and the processor calculates a stride rate of the user for each of a plurality of successive pedal-crank strides of a human user during an athletic activity.

In some embodiments, the athletic activity is cycling, and the processor determines, at each of a plurality of times during a ride, whether the user is coasting.

In some embodiments, the athletic activity is cycling, and the processor determines, at which of a plurality of times during a ride, whether the user is backpedaling, and if so, begins a calculation of forward pedaling performance or ends the calculation of forward pedaling performance that began at a prior determination of backpedaling.

In some such embodiments, the processor determines a count of how many backpedaling strokes, or the speed of backpedaling, or spacing backpedaling counts with coasting, or the angular magnitude of portions of backpedaled strokes were done (in some embodiments, each different type of backpedaling signals a different circumstance or parameter to the system's processor) to allow the bicyclist to indicate riding conditions that are not readily detected by other sensors (such as GPS), such as signaling to the processor the presence of a headwind, crosswind, rain storm or automobile or train traffic that hinders a portion of a ride, or of a tailwind that assists a portion of the ride.

In some embodiments, the backpedaling parameters are sensed or determined by the processor, which changes the visual and/or audible feedback to the user so that user can check or verify that the processor has started or ended some parameter-gathering function, such as tracking a portion of a ride during which the bicyclist encountered a headwind, tailwind, or crosswind. In some embodiments, the competitively tracked parameters during a game or competition are adjusted or handicapped based on the headwind, tailwind, or crosswind conditions encountered by different riders in different terrains.

In some embodiments, the athletic activity is cycling, the processor determines, at which of a plurality of times during a ride, whether the user is backpedaling, and if so, begins a calculation of forward pedaling performance or ends the calculation of forward pedaling performance that began at a prior determination of backpedaling, and the processor communicates to another system of another human user each time an instance of backpedaling has begun or ended for a purpose of a game or competition.

In some embodiments, the athletic activity is cycling, and the processor determines, at which of a plurality of times during a ride, whether the user is backpedaling, and if so, detecting how many backpedaling determinations were made in close succession, such that different competitive activities are signaled, to a corresponding processor associated with each of at least one other user, based on how many backpedaling instances in close succession were detected.

In some embodiments, a braking sensor is provided and operatively coupled to the processor, wherein the braking sensor is operative to allow the processor to receive parameters from the bicyclist (such as the bicyclist tapping on the brakes, one or two or more times, wherein the count of brake tapping is interpreted by the system's processor to start or end some process, in order to signal such things (as with backpedaling) as headwinds, crosswinds, tailwinds rain drizzling or storming, traffic, route detours, and the like.

In some embodiments, the processor is located in the foot-mounted sensor module, and the output device is a handlebar-mounted bicycle computer having a display that wirelessly receives and visually presents data based on calculated foot angles.

Some embodiments further include a plurality of additional sensors located in the personal electronic device, wherein the plurality of additional sensors in the personal electronic device include a global position sensor (GPS) sensor, and wherein the personal electronic device includes non-volatile storage into which GPS locations are stored with correlation data to corresponding stride data also stored in the non-volatile storage, and wherein the stride data is based on data from the foot-mounted sensor module.

In some embodiments, the athletic activity is running.

In some embodiments, the present invention provides a method of providing human perceptible behavior-modification feedback to a user, and a corresponding non-transitory computer-readable medium having instructions stored thereon for causing a suitably programmed computer processor system that includes an output device to execute the method of providing human perceptible behavior-modification feedback to a user, the method including: receiving a plurality of accelerometer-sensor and gyroscope-sensor data representing at least two orthogonal acceleration directions and at least one rotational directions; calculating foot angles at each of a plurality of successive positions within each of a plurality of strides of a human user during an athletic activity; and outputting human-perceptible indications based on the calculated foot-angle data.

In some embodiments of the method and corresponding non-transitory computer-readable medium, the output device includes a display, and wherein the computer-readable medium further includes instructions such that the method further includes: outputting graphical indications of calculated foot angle at a plurality of positions during each stride of a human user.

In some embodiments of the method and corresponding non-transitory computer-readable medium, the output device includes at least one audio output device, and wherein the computer-readable medium further including instructions such that the method further includes: outputting audible indications of calculated foot angle at a plurality of positions during each stride of a human user.

In some embodiments of the method and corresponding non-transitory computer-readable medium, the athletic activity is cycling.

In some embodiments of the method and corresponding non-transitory computer-readable medium, the athletic activity is cycling, wherein the plurality of successive positions within each of the plurality of strides of the human user correspond to at least three o'clock positions of a pedal crank of a bicycle, and wherein the outputting of human-perceptible indications based on the calculated foot-angle are based on calculated foot angle at each one of the at least three o'clock positions of the pedal crank.

In some embodiments of the method and corresponding non-transitory computer-readable medium, wherein the athletic activity is cycling, wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and wherein the outputting of human-perceptible indications based on the calculated foot-angles are based on calculated foot angle at each one of the 12-o'clock position, the 3-o'clock position, the 6-o'clock position, and the 9-o'clock position of the pedal crank.

In some embodiments of the method and corresponding non-transitory computer-readable medium, the athletic activity is cycling, wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a comparison of the calculated foot angles of the user to a predetermined desired or "ideal" foot angle at each of the four o'clock positions.

In some embodiments of the method and corresponding non-transitory computer-readable medium, the athletic activity is cycling, wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions as compared to a closeness comparison of another user's calculated foot angle relative to an "ideal" foot angle at each of the four o'clock positions, and wherein the outputting of human-perceptible indications includes presenting a human perceptible indication of whether the user has a closer comparison to the "ideal" foot angles relative to the other user's comparison.

In some embodiments of the method and corresponding non-transitory computer-readable medium, the athletic activity is cycling, wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions at each of a plurality of geographical locations of a current bicycle ride along a first bicycle route as compared to a closeness comparison of the user's calculated foot angle relative to the "ideal" foot angle at each of the four o'clock positions at each of the plurality of geographical locations along the first bicycle route during a prior bicycle ride, and wherein the outputting of human-perceptible indications includes presenting a human perceptible indication at a plurality of geographical locations during the current bicycle ride of whether the user has a closer comparison to the "ideal" foot angles relative to the user's foot angles at the same locations during the prior bicycle ride.

In some embodiments of the method and corresponding non-transitory computer-readable medium, the athletic activity is cycling, and wherein the computer-readable medium further includes instructions such that the method further includes: calculating and outputting a stride rate of the user for each of a plurality of successive pedal-crank strides of a human user during an athletic activity.

In some embodiments of the method and corresponding non-transitory computer-readable medium, the athletic activity is cycling, and wherein the computer-readable medium further includes instructions such that the method further includes: determining, at each of a plurality of times during a ride, whether the user is coasting.

In some embodiments of the method and corresponding non-transitory computer-readable medium, the athletic activity is cycling, and wherein the computer-readable medium further includes instructions such that the method further includes: determining, at which of a plurality of times during a ride, whether the user is backpedaling, and if so, begins a calculation of forward pedaling performance or ends the calculation of forward pedaling performance that began at a prior determination of backpedaling.

In some embodiments of the method and corresponding non-transitory computer-readable medium, the athletic activity is cycling, and wherein the computer-readable medium further includes instructions such that the method further includes: determining, at which of a plurality of times during a ride, whether the user is backpedaling, and if so, begins a calculation of forward pedaling performance or ends the calculation of forward pedaling performance that began at a prior determination of backpedaling, and communicating to another system of another human user each time an instance of backpedaling has begun or ended for a purpose of a game or competition.

In some embodiments of the method and corresponding non-transitory computer-readable medium, the athletic activity is cycling, and wherein the computer-readable medium further includes instructions such that the method further includes: determining, at which of a plurality of times during a ride, whether the user is backpedaling, and if so, detecting how many backpedaling determinations were made in close succession, such that different competitive activities are signaled, to a corresponding processor system associated with each of at least one other user, based on how many backpedaling instances in close succession were detected.

In some embodiments of the method and corresponding non-transitory computer-readable medium, the athletic activity is cycling, and wherein the computer-readable medium further includes instructions such that the method further includes: determining a count of how many backpedaling strokes, or the speed of backpedaling, or spacing backpedaling counts with coasting, or the angular magnitude of portions of backpedaled strokes were done (in some embodiments, wherein each different type of backpedaling signals a different circumstance or parameter to the processor system) to allow the bicyclist to indicate riding conditions that are not readily detected by other sensors (such as GPS), such as signaling to the processor system the presence of a headwind, crosswind, rain storm or automobile or train traffic that hinders a portion of a ride, or of a tailwind that assists a portion of the ride.

In some embodiments of the method and corresponding non-transitory computer-readable medium, the athletic activity is cycling, and wherein the computer-readable medium further includes instructions such that the method further includes: determining backpedaling parameters; and changing visual and/or audible feedback to the user based on the backpedaling parameters so that user can check or verify that the processor system has started or ended some parameter-gathering function, such as tracking a portion of a ride during which the bicyclist encountered a headwind, tailwind, or crosswind. In some such embodiments, competitively tracked parameters during a game or competition are adjusted or handicapped based on the headwind, tailwind, or crosswind conditions encountered by different riders in different terrains.

In some embodiments of the method and corresponding non-transitory computer-readable medium, the processor system is located in the foot-mounted sensor module, and wherein the output device is a handlebar-mounted bicycle computer having a display that wirelessly receives and visually presents data based on calculated foot angles.

In some embodiments of the method and corresponding non-transitory computer-readable medium, the method further includes receiving data from a plurality of additional sensors located in the user's personal electronic device, wherein the plurality of additional sensors in the personal electronic device include a global position sensor (GPS) sensor, and wherein the personal electronic device includes non-volatile storage into which GPS locations are stored with correlation data to corresponding stride data also stored in the non-volatile storage, and wherein the stride data is based on data from the foot-mounted sensor module.

In some embodiments, the present invention provides an apparatus that includes a foot-mounted sensor module that includes at least two accelerometer sensors to provide acceleration measurements in at least two orthogonal directions and at least two gyroscope sensors to provide rotational or gyroscopic measurements around at least one axial direction; a portable personal electronic device that wirelessly receives acceleration data representing the acceleration measurements in at least two orthogonal directions from the foot-mounted sensor module and rotational data representing the rotational or gyroscopic measurements; a processor that calculates foot angles at a plurality of successive positions within each of a plurality of strides of a human user during an athletic activity based on the received acceleration data and rotational data; and an output device in the personal electronic device that presents human-perceptible indications based on the calculated foot-angle data.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
    a portable personal electronic device that wirelessly receives acceleration data and rotational data from a foot-mounted sensor module that includes at least two accelerometer sensors to provide the acceleration data representing acceleration measurements in at least two orthogonal directions and at least one gyroscope sensor to provide the rotational data representing rotational or gyroscopic measurements around at least one axial directions;
    a processor that calculates foot angles at a plurality of successive positions within each of a plurality of strides of a human user during an athletic activity based on the received acceleration data and rotational data, wherein the processor includes:
        digital-filter algorithms that are applied to the acceleration data to obtain top-dead-center (TDC), right-hand (RH), bottom-dead-center (BDC) and left-hand (LH) time values, and
        a low-pass filter that is applied to the rotational data to obtain low-pass-filtered rotational data that includes gyro-drift data,
    wherein the processor calculates drift-filtered gyro data from differences between the rotational data and the low-pass-filtered rotational data in order to remove gyro drift, and wherein the processor uses the TDC, RH, BDC and LF time values to calculate foot angle data from the drift-filtered gyro data; and
        an output device in the personal electronic device that presents human-perceptible indications based on the calculated foot-angle data.

2. The apparatus of claim 1, wherein the output device includes a display that outputs graphical indications of calculated foot angle at a plurality of positions during each stride of a human user.

3. The apparatus of claim 1, wherein the output device includes at least one audio output device that outputs audible indications of calculated foot angle at a plurality of positions during each stride of a human user.

4. The apparatus of claim 1,
    wherein the athletic activity is cycling,
    wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and
    wherein the human-perceptible indications based on the calculated foot-angles are based on calculated foot angle at each one of the 12-o'clock position, the 3-o'clock position, the 6-o'clock position, and the 9-o'clock position of the pedal crank and on a comparison of the calculated foot angles of the user to a predetermined desired or "ideal" foot angle at each of the four o'clock positions.

5. The apparatus of claim 1,
    wherein the athletic activity is cycling,
    wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, wherein the human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions as compared to a closeness comparison of another user's calculated foot angle relative to an "ideal" foot angle at each of the four o'clock positions, and wherein the output device presents a human perceptible indication of whether the user has a closer comparison to the "ideal" foot angles relative to the other user's comparison.

6. The apparatus of claim 1, further comprising:
a foot-mounted sensor module that includes at least two accelerometer sensors to provide acceleration measurements in at least two orthogonal directions and at least two gyroscope sensors to provide rotational or gyroscopic measurements around at least one axial direction, wherein the foot-mounted sensor module wirelessly transmits the acceleration data based on the acceleration measurements and the rotational data based on the rotational or gyroscopic measurements.

7. The apparatus of claim 1, wherein the calculation of foot angle data further includes an adjustment for a sensor mount angle.

8. The apparatus of claim 1,
wherein the processor calculates an interpretation of the user's athletic form, and
wherein the processor communicates the interpretation of the user's form to another system of another human user for a game or competition.

9. A non-transitory computer-readable medium having instructions stored thereon for causing a suitably programmed computer processor system that includes an output device to execute a method of providing human perceptible behavior-modification feedback to a user, the method comprising:
receiving a plurality of accelerometer-sensor and gyroscope-sensor data representing at least two orthogonal acceleration directions and at least one rotational directions;
calculating foot angles at each of a plurality of successive positions within each of a plurality of strides of a human user during an athletic activity, wherein the calculating includes:
applying digital-filter algorithms to the acceleration data to obtain top-dead-center (TDC), right-hand (RH), bottom-dead-center (BDC) and left-hand (LH) time values, low-pass filtering the rotational data to obtain low-passed rotational data that includes gyro-drift data,
obtaining drift-filtered gyro data from differences between the rotational data and the low-passed rotational data to remove gyro drift, and
calculating foot angles from the drift-filtered gyro data based on the TDC, RH, BDC and LF time values; and
outputting human-perceptible indications based on the calculated foot-angle data.

10. The non-transitory computer-readable medium of claim 9, wherein the output device includes a display, and wherein the computer-readable medium further includes instructions such that the method further comprises:
outputting graphical indications of calculated foot angle at a plurality of positions during each stride of a human user.

11. The non-transitory computer-readable medium of claim 9, wherein the output device includes at least one audio output device, and wherein the computer-readable medium further comprising instructions such that the method further comprises:
outputting audible indications of calculated foot angle at a plurality of positions during each stride of a human user.

12. The non-transitory computer-readable medium of claim 9,
wherein the athletic activity is cycling,
wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride, and
wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a comparison of the calculated foot angles of the user to a predetermined desired or "ideal" foot angle at each of the four o'clock positions.

13. The non-transitory computer-readable medium of claim 9,
wherein the athletic activity is cycling,
wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride,
wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions as compared to a closeness comparison of another user's calculated foot angle relative to an "ideal" foot angle at each of the four o'clock positions, and
wherein the outputting of human-perceptible indications includes presenting a human perceptible indication of whether the user has a closer comparison to the "ideal" foot angles relative to the other user's comparison.

14. The non-transitory computer-readable medium of claim 9,
wherein the athletic activity is cycling,
wherein the plurality of successive positions within each of the plurality of strides of the human user include a 12-o'clock position of a pedal crank of a bicycle, a 3-o'clock position of the pedal crank, a 6-o'clock position of the pedal crank, and a 9-o'clock position of the pedal crank during a single stride,
wherein the outputting of human-perceptible indications based on the calculated foot-angles are based on calculated foot angle at each one of the 12-o'clock position, the 3-o'clock position, the 6-o'clock position, and the 9-o'clock position of the pedal crank and on a closeness comparison of the user's calculated foot angles of the user relative to an "ideal" foot angle at each of the four o'clock positions at each of a plurality of geographical locations of a current bicycle ride along a first bicycle route as compared to a closeness comparison of the user's calculated foot angle relative to the "ideal" foot angle at each of the four o'clock positions at each of the plurality of geographical locations along the first bicycle route during a prior bicycle ride, and wherein the outputting of human-perceptible indications includes presenting a human perceptible indication at a plurality of geographical locations during the current bicycle ride of whether the user has a closer comparison to the "ideal" foot angles relative to the user's foot angles at the same locations during the prior bicycle ride.

15. The non-transitory computer-readable medium of claim 9, wherein the calculating of foot angle data further includes an adjustment for a sensor mount angle.

16. The non-transitory computer-readable medium of claim 9, wherein the processor calculates an interpretation of the user's athletic form, and wherein the processor communicates the interpretation of the user's form to another system of another human user for a game or competition.

17. A non-transitory computer-readable medium having instructions stored thereon for causing a suitably programmed computer processor system that includes an output device to execute a method of providing human perceptible behavior-modification feedback to a user, the method comprising:

receiving a plurality of accelerometer-sensor and gyroscope-sensor data representing at least two orthogonal acceleration directions and at least one rotational directions:

calculating foot angles at each of a plurality of successive positions within each of a plurality of strides of a human user during an athletic activity;

outputting human-perceptible indications based on the calculated foot-angle data, wherein the athletic activity is cycling, and wherein the computer-readable medium further includes instructions such that the method further comprises:

determining, at each of a plurality of times during a ride, whether the user is backpedaling, and if so, begins a calculation of forward pedaling performance or ends the calculation of forward pedaling performance that began at a prior determination of backpedaling, and communicating to another system of another human user each time an instance of backpedaling has begun or ended for a purpose of a game or competition.

18. A non-transitory computer-readable medium having instructions stored thereon for causing a suitably programmed computer processor system that includes an output device to execute a method of providing human perceptible behavior-modification feedback to a user, the method comprising:

receiving a plurality of accelerometer-sensor and gyroscope-sensor data representing at least two orthogonal acceleration directions and one or more rotational directions;

calculating foot angles at each of a plurality of successive positions within each of a plurality of strides of a human user during an athletic activity;

outputting human-perceptible indications based on the calculated foot-angle data, wherein the athletic activity is cycling, and wherein the computer-readable medium further includes instructions such that the method further comprises:

determining backpedaling parameters; and changing visual and/or audible feedback to the user based on the backpedaling parameters so that user can check or verify that the processor system has started or ended some parameter-gathering function.

19. The non-transitory computer-readable medium of claim 18, wherein the computer-readable medium further includes instructions such that the method further comprises:

determining, at which of a plurality of times during a ride, whether the user is backpedaling, and if so, detecting how many backpedaling determinations were made in close succession, such that different competitive activities are signaled, to a corresponding processor system associated with each of at least one other user, based on how many backpedaling instances in close succession were detected.

20. The non-transitory computer-readable medium of claim 19, where wherein the computer-readable medium further includes instructions such that the method further comprises:

determining a count of how many backpedaling strokes, or the speed of backpedaling, or spacing backpedaling counts with coasting, or the angular magnitude of portions of backpedaled strokes were done, wherein each different type of backpedaling signals a different circumstance or parameter to the processor system to allow the bicyclist to indicate riding conditions that are not readily detected by global positioning sensors, including signaling to the processor a presence of at least two of: a headwind, a crosswind, a rain storm, automobile traffic, and train traffic that hinders a portion of a ride, or of a tailwind that assists a portion of the ride.

21. The non-transitory computer-readable medium of claim 18, wherein the athletic activity is cycling, and wherein the computer-readable medium further includes instructions such that the method further comprises:

wherein the backpedaling parameters cause the processor system to start or end some parameter-gathering function for a portion of a ride, and wherein competitively tracked parameters during a game or competition are adjusted or handicapped based on conditions encountered by different riders in different terrains.

* * * * *